(12) United States Patent
Lucas et al.

(10) Patent No.: US 7,022,819 B2
(45) Date of Patent: Apr. 4, 2006

(54) ISOLATED NUCLEIC ACID MOLECULE CODING FOR TUMOR REJECTION ANTIGEN PRECURSORS MAGE-C1 AND MAGE-C2 AND USES THEREOF

(75) Inventors: Sophie Lucas, Brussels (BE); Charles De Smet, Brussels (BE); Thierry Boon-Falleur, Brussels (BE)

(73) Assignee: Ludwig Institute for Cancer Research, New York, NY (US)

( * ) Notice: Subject to any disclaimer, the term of this patent is extended or adjusted under 35 U.S.C. 154(b) by 680 days.

(21) Appl. No.: 10/160,237

(22) Filed: Jun. 4, 2002

(65) Prior Publication Data

US 2003/0170256 A1    Sep. 11, 2003

Related U.S. Application Data

(60) Division of application No. 09/066,281, filed on Apr. 24, 1998, now Pat. No. 6,475,783, which is a continuation-in-part of application No. 08/845,528, filed on Apr. 25, 1997, now Pat. No. 6,027,924.

(51) Int. Cl.
*C07K 14/00* (2006.01)

(52) U.S. Cl. ............... 530/350; 424/277.1; 424/184.1; 424/185.1; 536/23.1

(58) Field of Classification Search ............... 530/350; 536/23.1; 424/184.1, 185.1, 277.1
See application file for complete search history.

(56) References Cited

U.S. PATENT DOCUMENTS

| | | |
|---|---|---|
| 4,889,806 A | 12/1989 | Olson |
| 5,342,774 A | 8/1994 | Boon |
| 5,405,940 A | 4/1995 | Boon |
| 5,462,871 A | 10/1995 | Boon-Falleur |
| 5,487,974 A | 1/1996 | Boon-Falleur |
| 5,554,506 A | 9/1996 | van der Bruggen |
| 5,554,724 A | 9/1996 | Melief |
| 5,750,395 A * | 5/1998 | Fikes et al. ............ 435/325 |

FOREIGN PATENT DOCUMENTS

WO    WO-94/03205    2/1994

OTHER PUBLICATIONS

Schmid S et al, 2001, J comparative Neurology, 430(2): 160-71.*
Conner et al, 1996, Mol Brain Res, 42: 1-17.*
MPSRCH search report, 2005, us-10-160-237-18.rai, pp. 3-4.*
DATABASE EMBL, Tumour rejection antigen MAGE-4 gene Database accession no. AAQ72482 XP002221384, Oct. 13, 1994.
DATABASE EMBL, MZ2-MEL antigen E precursor, Database accession no. AAT05086 XP002221385, Sep. 8, 1995.
Lucas Sophie et al., Identification of a new MAGE gene with tumor-specific expression by representational difference analysis, Cancer Research, vol. 58, No. 4, pp. 743-752, Feb. 15, 1998.
Chen et al., Identification of multiple cancer/testis antigens by allogenic antibody screening of a melanoma cell line library. Proceedings of the National Academy of Sciences of USA, National Academy of Science. vol. 95, pp. 6919-6923, Jun. 1998.
Townsend et al., "The Epitopes of Influenza Nucleoprotein Recognized by Cytotoxic T Lymphocytes Can Be Defined With Short Synthetic Peptides", Cell, 44: 959-968 (1986).
Bjorkman et al., "The foreign antigen binding site and T cell recognition regions of class I histocompatibility antigen", Nature, 329: 512-518 (1987).
Van der Bruggen et al., "A Gene Encoding an Antigen Recognized by Cytolytic T Lymphocytes on a Human Melanoma", Science 254: 1643-1647 (1991).
Traversari et al., "A Nonapeptide Encoded by Human Gene MAGE-1 Is Recognized on HLA-A1 by Cytolytic T Lymphocytes Directed Againstst Tumor Antigen MZ2-E", J. Exp. Med. 176: 1453-1457 (1992).
Ruppert et al., "Prominent Role of Secondary Anchor Residues in Peptide Binding to HLA-A2.1 Molecules". Cell 74: 929-937 (1993).

(Continued)

*Primary Examiner*—Susan Ungar
*Assistant Examiner*—Minh-Tam Davis
(74) *Attorney, Agent, or Firm*—Fulbright & Jaworski

(57) ABSTRACT

The invention relates to isolated nucleic acid molecules which code for antigens expressed by tumor cells which maybe recognized by cytotoxic T cells, leading to lysis of the tumor cells which express it. This invention also relates to vectors which are designed to encode the antigen expressed by tumor cells and also to cells transfected by the nucleic acid molecules or vectors which comprise the nucleic acid molecules. Various therapeutic and diagnostic uses arising out of the properties of the nucleic acid molecules and the antigens for which these code are also part of this invention.

2 Claims, 14 Drawing Sheets

OTHER PUBLICATIONS

Celis et al., "Induction of anti-tumor cytotoxic T lymphocytes in normal humans using primary cultures and synthetic peptide epitopes", Proc. Natl. Acad. Sci. USA 91: 2105-2109 (1994).

Coulie et al., "A New Gene Coding For A Differentiation Antigen Recognized by Autologous Cytolytic T Lymphocytes on HLA-A2 Melanomas", J. Exp. Med. 180: 35-42 (1994).

Engelhard et al., "Structure of Peptides Associated With Class I and Class II MHC Molecules", Ann. Rev. Immunol. 12: 181-207 (1994).

DeSmet et al., "Sequence and expression pattern of the human MAGE-2 gene", Immunogenitc 39: 121-129 (1994).

Ding, et al., "Cloning And Analysis of MAGE-1 Related Genes", Biochem & Biophys. Res. Commun. 202(1): 549-555 (1994).

Van der Bruggen, et al., "A peptide encoded by human gene MAGE-3 and presented by HLA-A2 induces cytolytic T lymphocytes that recognize tumor cells expressing MAGE-3", Eur. J. Immunol. 24: 3038-3043 (1994).

A.G. Dalgleish, et al., "Tumor Immunology", Cancer Clinical Science in Practice, (1994).

De Plaen, et al., "Structure, chromosomal localization, and expression of 12 genes of the Mage family", Immunogenetics 40: 360-369 (1994).

M. Hubank, et al., "Identifying differences in mRNA expression by representational difference analysis of cDNA", Nucleic Acids Research 22: 25:5640-5648 (1994).

De Plaen et al., Accessio No. U10685.

Harris et al. "J. of The Am Society of Nephrology" 65: 1125-1133 (1995).

Ahn et al. Nature Genetics 3(4): 283-291 (1993).

Cawthon et al. Genomics 9(3): 446-460 (1991).

De Plaen Immunogenetics, 40: 360-369 (1994).

Bowie et al., Science 257: 1306-1310 (1990).

Burgess et al. J. Of Cell Bio. 111: 2129-2138 (1990).

Lazar et al. Molecular and Cellular Biology, 8: 1247-1252 (1988).

Bork, Genome Research, 10: 398-400 (2000).

Sambrook et al., "Molecular Cloning", A Laboratory Manual, 2nd Edition, Cold Spring Harbor Press, Cold Spring Harbor, p. 16.3-16.4.

* cited by examiner

Figure 1(A)

| | |
|---|---|
| G*GATC*GTCTCAGGTCAGCGGAGGGA | 25 |
|                     SL33 | |
| GGAGACTTATAGACCTATCCAGTCT | 50 |
| TCAAGGTGCTCCAGAAAGCAGGAGT | 75 |
| TGAAGACCTGGGTGTGAGGACACA | 100 |
| TACATCCTAAAAGCACCACAGCAGA | 125 |
| GGAGGCCCAGGCAGTGCCAGGAGTC | 150 |
| AAGGTTCCAGAAGACAAACCCCCT | 175 |
| AGGAAGACAGGCGACCTGTGAGGCC | 200 |
| CTAGAGCACCACCTTAAGAGAAGAA | 225 |
|             SL34 | |
| GAGCTGTAAGCCGGCCTTTGTCAGA | 250 |
| GCCATCATGGGGGACAAGGATATGC | 275 |
| CTACTGCTGGGATGCCGAGTCTTCT | 300 |
| CCAGAGTTCCTCTGAGAGTCCTCAG | 325 |
| AGTTGTCCTGAGGGGGAGGACTCCC | 350 |
| AGTCCTCTCCAGATTCCCCAGAG | 375 |
| TTCTCCTGAGAGCGACGACACCCTG | 400 |
| TATCCTCTCCAGAGTCCTCAGAGTC | 425 |
| GTTCTGAGGGGGAGGACTCCTCGGA | 450 |
| TCCTCTCCAGAGACCTCCTGAGGGG | 475 |
| AAGGACTCCCAGTCTCCTCTCCAGA | 500 |
| TTCCCCAGAGTTCTCCTGAGGGCGA | 525 |
| CGACACCCAGTCTCCTCTCCAGAAT | 550 |
| TCTCAGAGTTCTCCTGAGGGGAAGG | 575 |
| ACTCCCTGTCTCCTCTAGAGATTTC | 600 |
| TCAGAGCCCTCCTGAGGGTGAGGAT | 625 |
| GTCCAGTCTCCTCTGCAGAATCCTG | 650 |
| CGAGTTCCTTCTTCTCCTCTGCTTT | 675 |
| ATTGAGTATTTTCCAGAGTTCCCCT | 700 |

Figure 1(B)

| Sequence | Position |
|---|---|
| GAGAGAACTCAGAGTACTTTTGAGG | 725 |
| GTTTTCCCCAGTCTCCTCTCCAGAT | 750 |
| TCCTGTGAGCTCCTCCTCCTCCTCC | 775 |
| ACTTTATTGAGTCTTTTCCAGAGTT | 800 |
| CCCCTGAGAGAACTCAGAGTACTTT | 825 |
| TGAGGGTTTTCCCAGTCTCTTCTC | 850 |
| CAGATTCCTATGACCTCCTCCTTCT | 875 |
| CCTCTACTTTATTGAGTATTTTCCA | 900 |
| GAGTTCTCCTGAGAGTGCTCAAAGT | 925 |
| ACTTTTGAGGGTTTTCCCCAGTCTC | 950 |
| CTCTCCAGATTCCTGGGAGCCCTC | 975 |
| CTTCTCCTCCACTTTACTGAGTCTT | 1000 |
| TTCCAGAGTTCCCCTGAGAGAACTC | 1025 |
| ACAGTACTTTTGAGGGTTTTCCCCA | 1050 |
| GTCTCCTCTCCAGATTCCTATGACC | 1075 |
| TCCTCCTTCTCCTCTACTTTATTGA | 1100 |
| GTATTTTCCAGAGTTCTCCTGAGAG | 1125 |
| TGCTCAAAGTACTTTTGAGGGTTTT | 1150 |
| CCCCAGTCTCCTCTCCAGATTCCTG | 1175 |
| GGAGCCCCTCCTTCTCCTCCACTTT | 1200 |
| ACTGAGTCTTTTCCAGAGTTCCCCT | 1225 |
| GAGAGAACTCACAGTACTTTTGAGG | 1250 |
| GTTTTCCCCAGTCTCCTCTCCAGAT | 1275 |
| TCCTATGACCTCCTCCTTCTCCTCT | 1300 |
| ACTTTATTGAGTATTTACAGAGTT | 1325 |
| CTCCTGAGAGTGCTCAAAGTGCTTT | 1350 |
| TGAGGGTTTTCCCCAGTCTCCTCTC | 1375 |
| CAGATTCCTGTGAGCTCCTCTTTCT | 1400 |

Figure 1(C)

```
CCTACACTTTATTGAGTCTTTTCCA    1425
GAGTTCCCCTGAGAGAACTCAGAGT    1450
ACTTTGAGGGTTTTCCCCAGTCTC     1475
CTCTCCAGATTCCTGTGACTCCTC     1500
CTCCTCCTCCTCCACTTTATTGAGT    1525
CTTTTCCAGAGTTCCCTGAGTGTA     1550
CTCAAGTACTTTGAGGTTTTCC       1575
CCAGTCTCCTCTCCAGATTCCTCAG    1600
AGTCCTCCTGAAGGGGAGAATACCC    1625
ATTCTCCTCCAGATTGTTCCAAG      1650
TCTTCCTGAGTGGGAGGACTCCCTG    1675
TCCTCACTACTTTCCTCAGAGCC      1700
CTCCTCAGGGGAGGACTCCTATC      1725
TCCTCACTACTTTCCTCAGAGCCCT    1750
CCTCAGGGGAGGACTCCTGTCTC      1775
CTCACTACTTTCCTCAGAGCCCTCA    1800
GGGGGAGGACTCCCTGTCTCCTCAC    1825
TACTTTCCTCAGAGCCCTCCTCAGG    1850
GGGAGGACTCCATGTCTCCTCTCTA    1875
CTTTCCTCAGAGTCCTCTTCAGGGG    1900
GAGGAATTCCAGTCTTCTCTCCAGA    1925
GCCTGTGAGCATCTGCTCCTCCTC     1950
CACTCCATCCAGTCTTCCCCAGAGT    1975
TTCCCTGAGAGTTCTCAGAGTCCTC    2000
CTGAGGGGCCTGTCCAGTCTCCTCT    2025
CCATAGTCCTCAGAGCCCTCCTGAG    2050
GGGATGCACTCCAATCTCCTCTCC     2075
AGAGTCCTGAGAGTGCTCCTGAGGG    2100
```

Figure 1(D)

| | |
|---|---|
| GGAGGATTCCCTGTCTCCTCTCCAA | 2125 |
| ATTCCTCAGAGTCCTCTTGAGGGAG | 2150 |
| AGGACTCCCTGTCTTCTCTCCATTT | 2175 |
| TCCTCAGAGTCCTCCTGAGTGGGAG | 2200 |
| GACTCCCTCTCCTCTCCACTTTC | 2225 |
| CTCAGTTTCCTCCTCAGGGGGAGGA | 2250 |
| CTTCCAGTCTTCTCTCCAGAGTCCT | 2275 |
| GTGAGTATCTGCTCCTCCTCCACTT | 2300 |
| CTTTGAGTCTTCCCCAGAGTTTCCC | 2325 |
| TGAGAGTCCTCAGAGTCCTCCTGAG | 2350 |
| GGGCCTGCTCAGTCTCCTCTCCAGA | 2375 |
| GACCTGTCAGCTCCTTCTTCTCCTA | 2400 |
| CACTTTAGCGAGTCTTCTCCAAAGT | 2425 |
| TCCCATGAGAGTCCTCAGAGTCCTC | 2450 |
| CTGAGGGGCCTGCCCAGTCTCCTCT | 2475 |
| CCAGAGTCCTGTGAGCTCCTTCCCC | 2500 |
| TCCTCCACTTCATCGAGTCTTTCCC | 2525 |
| AGAGTTCTCCTGTGAGCTCCTTCCC | 2550 |
| CTCCTCCACTTCATCGAGTCTTTCC | 2575 |
| AAGAGTTCCCCTGAGAGTCCTCTCC | 2600 |
| AGAGTCCTGTGATCTCCTTCTCCTC | 2625 |
| CTCCACTTCATTGAGCCCATTCAGT | 2650 |
| GAAGAGTCCAGCAGC<u>CCAGTAGATG</u> | 2675 |
| <center>SL26</center> | |
| <u>AATATACAAGTT</u>CCTCAGACACCTT | 2700 |
| GCTAGAGAGTGATTCCTTGACAGAC | 2725 |
| AGCGAGTCCTTGATAGAGAGCGAGC | 2750 |
| CCTTGTTCACTTATACACTGGATGA | 2775 |
| AAAGGTGGACGAGTTGGCGCGGTTT | 2800 |

Figure 1(E)

| | |
|---|---|
| CTTCTCCTCAAATATC<u>AAGTGAAGC</u> | 2825 |
| <u>SL27</u> | |
| <u>AGCCTATCA</u>CAAAGGCAGAGATGCT | 2850 |
| GACGAATGTCATCAGCAGGTACACG | 2875 |
| GGCTACTTTCCTGT*GATC*TTCAGGA | 2900 |
| AAGCCCGTGAGTTCATAGAGATACT | 2925 |
| TTTTGGCATTTCCTGAGAGAAGTG | 2950 |
| GACCCTGATGACTCCTATGTCTTTG | 2975 |
| TAAACACATTAGACCTCACCTCTGA | 3000 |
| GGGGTGTCTGAGTGATGAGCAGGGC | 3025 |
| ATGTCCCAGAACCGCCTCCTGATTC | 3050 |
| TTATTCTGAGTATCATCTTCATAAA | 3075 |
| GGGCACCTATGCCTCTGAGGAGGTC | 3100 |
| ATCTGGGATGTGCTGAGTGGAATAG | 3125 |
| GGGTGCGTGCTGGGAGGGAGCACTT | 3150 |
| TGCCTTTGGGGAGCCCAGGGAGCTC | 3175 |
| CTCACTAAAGTTTGGGTGCAGGAAC | 3200 |
| ATTACCTAGAGTACCGGGAGGTGCC | 3225 |
| CAACTCTTCTCCTCCTCGTTACGAA | 3250 |
| TTCCTGTGGGGTCCAAGAGCTCATT | 3275 |
| CAGAAGTCATTAAGAGGAAAGTAGT | 3300 |
| AGAGTTTTTGGCCATGCTAAAGAAT | 3325 |
| ACCGTCCCTATTACCTTTCCATCCT | 3350 |
| CTTACAAGGATGCTTTGAAAGATGT | 3375 |
| GGAAGAGAGAGCCCAGGCCATAATT | 3400 |
| GACACCACAGATGATTCGACTGCCA | 3425 |
| CAGAAAGTGCAAGCTCCAGTGTCAT | 3450 |
| GTCCCCAGCTTCTCTT CTGAGTGA | 3475 |
| AGTCTAGGGCAGATTCTTCCCTCTG | 3500 |

Figure 1(F)

```
AGTTTGAAGGGGGCAGTCGAGTTTC        3525
TACGTGGTGGAGGGCCTGGTTGAGG        3550
CTGGAGAACACAGTGCTATTTGC          3575
ATTTCTGTTCCATATGGGTAGTTAT        3600
GGGGTTACCTGTTTACTTTTGGG          3625
TATTTTCAAATGCTTTTCCTATTA         3650
ATAACAGGTTTAAATAGCTTCAGAA        3675
TCCTAGTTTATGCACATGAGTCGCA        3700
CATGTATTGCTGTTTTCTGGTTTA         3725
AGAGTAACAGTTTGATATTTTGTAA        3750
AAACAAAACACACCCAAACACACC         3775
ACATTGGGAAAACCTTCTGCCTCAT        3800
TTTGTGATGTGTCACAGGTAATGT         3825
GGTGTTACTGTAGGAATTTTCTTGA        3850
AACTGTGAAGGAACTCTGCAGTTAA        3875
ATAGTGGAATAAAGTAAAGGATTGT        3900
TAATGTTTGCATTCCTCAGGTCCT         3925
TTAGTCTGTTGTTCTTGAAAACTAA        3950
AGATACATACCTGGTTTGCTTGGCT        3975
TACGTAAGAAAGTAGAAGAAAGTAA        4000
ACTGTAATAAATAAAAAAAAAAAA         4025
AAAAAA                           4031
```

FIG. 2(A)

```
        exonⅠ┐
       ┌exonⅠ                                                       ┌intronⅠ
A1     CCATTCTGAGGGACGGGGTA GAGTTCGGCCGAAGGAACCT GACCCAGGCTCTGTGAGGAG GCAAGgtgag//............................//..      27
C1                                                                   GGATCGT CTCAGGTCAGCGGGAGGGAGG tgagacagtatcctcaggtc
A1     .............................//ctg gagctccaggaaccaggcag tgaggccttggt..........c                          115
C1     AGACTTATAGACCTATCCAG TCTTCAAGgt//......//cag GTGCTCCAGAAAGCAGGAGT TGAAGACCTGGGTGTGAGGG ACACATACATCCTAAAAGCA
                                 exonⅡ└ └intronⅠ └exonⅡ acaggacacataggactcca
A1     acagagcagaggatgcacag ggtgtgccagcagtgaatgt tt.......gccctgaatgca caccaagggcccccacctgcc                      70
C1     CCAGCAGCAGGAGGGCCCAG GCAGTGCCAGGTCAAGgt gagtgcacgacctgactgtg taccagggccgtaccccca gaaacagtgtcagacctggc    158
                            exonⅡ└ └intronⅡ                                                      intronⅡ┐ ┌exonⅡ

A1     cagagtctggcctcacctcc ctactgtcagtcctgtagaa tcgac-ctctgctggccggc tgtaccctga-gtaccctct cacttcctccttcagGTTTT  158
C1     agcaccggccccctgtagcca ccactgtcattcctggtgcc tcatggctctgctgccage tgtgccccgaggtgcttct cgcgtccttctacagGTTCC  258
                                                                            exonⅡ└ └intronⅡ   intronⅡ┐ ┌exonⅢ
                                                                                                             M gcctttgttagagtctccaa
A1     CAGGGGACAGGGCCAACCCAG AGGACAGGATTCCCTGAGG CCACAGAGGAGCACC----A AGGAGAAGATCTgtaagtag                        188
C1     CAGAAGAGACAAACCCCCTAGG AAGACAGGCGACCTGTGAGG CCCTAGAGCACCACCTTAAG AGAAGAAGAGCTGTAAGCCG GCCTTTGTCAGAGCCATCAT  258
                                                                                 exonⅢ└ └intronⅢ                 M A1     ggttcag-ttctcagctgag gcctctcacacactccctct ctccc-cagGCCTGTGGGTC TTCATTG-CCCAGCTCCTGC CCACACTCCTGCCTGCTGCC      28
C1     GGgtgagttctcagctgag gccactgcactgtcccctct ctccctcagtcctgtgggat cccatcatacctattcgtgt tcacacgtttacctgctgct   286
       exonⅢG┘ └intronⅢ                                                                          A L G L V C V M   S L E Q R S L   H C K P E E A   L E A Q Q E   A L G L V C V
A1     CT--GACGAGAGTCATCATG TCTCTTGAGCAGAGAGGAGTCT GCACTGCAAGCCTGAGGAAG CCCTTGAGGCCCAACAAGAG GCCCTGGGCCTGGTGTGTGT  386
C1     cctgaacaatattcatcatg cctctcttctaaaccttcc acgccccagctttgagcaag gcttccagaaggcaattttc atactggagttggtagatgc Q S P Q G A    Q A A T S S S    S P L V L G    T L E E V P T    A G S T D P P
A1     CCCAGAGTCCTCAGGGAGCC CCCAGAGTCCTCAGGGAGCC                                                                  61
C1     GCAGGCTGCCACCTCCTCCT CCTCTCCTCTGGTCCTGGGC ACCCTGGAGGAGGTGCCCAC TGCTGGGGTCAACAGATCCTC CCCAGAGTCCTCAGGGAGCC  386

S A F P T T I    N F T R Q R Q    P
A1     TCCGGCCTTTCCCACTACCAT CAACTTCACTCGACAGAGGC AACCC......................................................   76
C1     agaggatccccca.......                                                                                     431
                                                   gatgaggaagaggag gaagcttcctccattttctc ttcctcttccactttttat
```

FIG. 2(B)

```
A1  ..............................................................................................  294
C1  tcccctcgtcctcctcctgt ttttcttctcatcctcatc ctcctctctgtcttctgcgtt ctccagGGGACAAGGATATG CCTACTGCTGCTGGGATGCCGAG
                                                                      ─┘    D  K  D  M   P  T  A  G  M  P  S   13
                                                              intron III  exon IV A1  TCTTCTCCAGAGTTCCTCTG AGAGTCCTCAGAGTTGTCCT GAGGGGGAGGACTCCCAGTC TCCTCTCCAGATTCCCCAGA GTTCTCCTGAGAGCGACGAC  394
    L  L  Q  S  S  S  E    S  P  Q  S   Y  P  E  G  E  D  S  Q  S   P  L  Q  I  P    Q  S   S  P  E  S  D  D   46

A1  ACCCTGTATCCTCTCCAGAG TCCTCAGAGTCGTTCTGAGG GGGAGGACTCCTCGGATCCT CTCCAGAGACCTCCTGAGGG GAAGGACTCCCAGTCTCCTC  494
    T  L  Y  P  L  Q  S    P    Q  S  R  S  E  G   E  D  S  S  D  P   L  Q  R    P  P  E  G   K  D  S  Q  S  P  L   80

A1  TCCAGAGATTCCCCAGAGTCT CCTGAGGGGCGACGACACCCA GTCTCCTCCTCCCAGAATTCTC AGAGTTCTCCTGAGGGGAAG GACTCCCTGTCTCCTCTAGA  594
    Q  I  P    Q  S  S   P  E  G  D  D  T  Q   S  P  L  Q  N  S    Q   S  S  P  E  G  K   D  S  L  S  P  L  E    113

A1  GATTTCTCAGAGGCCCTCCTG AGGGTGAGGATCCAGAGG AGGGTGAGGAGGATGTCCAGTCT CCTCTGCAGAATCCTGACGAG TTCCTTCTCTCCTCTGCTT  694
    I  S    Q  S  P  P  E    G  E  D  V  Q  S    P  L  Q  N  P    A  S    S  F  F  S  S  A  L  L    146

A1  TCCCCTGAGAGTATTCAAAG TCCTTTTGAGGGTTTTCCCC AGTCTGTTCTCCAGAGTCCAGA GTGAGCGGCGCCTCCTC CACTTTAGTGAGTATTTCC  794
    S  P  E    S  I    Q    S   P  F  E  G  F  P  Q    S  V  L  Q  I  P    V  S  A  A  S  S    T  L  V  S  I  F  Q   180

A1  AGAGTTCCCCTGAGAGTACT CAAAGTCCTTTTGAGGGTTT TCCCAGTCTCCACTCCAGA TTCCTGTGAGCCGGTCCTTC TCCTCCACTTATTGAGTAT  894
    S  S  P  E  S  T    Q    S  P  F  E  G  F    P  Q  S  P  L  Q  I  P    V  S  R  S  F   S  S  T  L  L  S  I    213

A1  TTTCCAGAGTTCCCCTGAGA GAAGTCAGAGAACTTCTGAG GGTTTTGCACAGTCTCCTCT CCAGATTCCTGTGAGCTCCT CCTGTCCTCCACTTTACTG  994
    F  Q  S    S  P  E  R    S  Q    R  T  S  E    G  F  A  Q  S  P  L   Q  I  P    V  S  S  S  S  S  T  L  L   246
```

FIG. 2(C)

```
A1  ......................................................................................
C1  AGTCTTTTCCAGAGTTCCCC TGAGAGAACTCAGAGTACTT TTGAGGGTTTTCCCCAGTCT CCACTCCAGATTCCTGTGAG CCGCTCCTTCTCTCCCACTT 1094
     S  L  F  Q  S   P   E  R  T  Q  S  T  F   E  G  F  P  Q  S   P  L  Q  I  P  V  S   R  S  F  S  S  T  L   280

A1  ......................................................................................
C1  AGTCTTTTCCAGAGTTCCCC TGAGAGAACTCAGAGTACTT TTGAGGGTTTTCCCCAGTCT CCACTCCAGATTCCTGTGAG CCGCTCCTTCTCTCCCACTT 1094
                                                                                                            313
    TATTGAGTATTTTCCAGAGT TCCCCTGAGAGAACTCAGAG TACTTTTGAGGGTTTTGCCC AGTCTCCTCTCCTCTTCCAGA GTGAGCTCCTCCTCCTCCTC 1194
     L  S  I  F  Q  S   S  P  E  R  T  Q  S   T  F  E  G  F  A  Q  S  P  L  Q  I  P  V  S   S  S  S  S  S   S

A1  ......................................................................................
C1  CACTTATTGAGTCTTTTTCC AGAGTTCCCCTGAGAGAACT CAGAGTACTTTTGAGGGTTT TCCCCAGTCTCTCTTCCAGA TTCCTATGACCTCCTCCTTC 1294
     T  L  L  I  E  S   L  F  Q  S  S  P  E   R  T  Q  S  T  F  E  G  F  P  Q  S  L  L  Q  I  P  M  T  S  S  F   346

A1  ......................................................................................
C1  TCCTCTACTTATTGAGTAT TTTCCAGAGTTCCCCTGAGA GTGCTCAAAGTACTTTTGAG GGTTTCCCCAGTCTCCTCT CCAGATTCCTGGGAGCCCCT 1394
     S  S  F  S  T  L   I  L  F  Q  S  S  P   E  S  A  Q  S  T  F  E  G  F  P  Q  S  P  L  Q   I  P  G  S  P  S   380

A1  ......................................................................................
C1  CCTTCCTCCTCCACTTACTG AGTCTTTTCCAGAGTATTTTACAGAGT TCTCCTGAGAGAACTCACAGAGT TGAGAGAACTCAGAGTACT TTGAGGGTTTCCCAGTC CCTCTCCTCCAGATTCCT CCTCCTCCAGATTCCTATGAC 1494
     F  S  S  T  L   S  L  F  Q  S  S  P   E  R  T  H  S  T  F  E  G  F  P  Q  S  P  L  Q  I  P  M  T   413

A1  ......................................................................................
C1  CTCCTCCTCCCACTT TATTGAGTATTTTACAGAGT TCTCCTGAGAGAACTCACAGAGT TGAGAGAACTCAGAGTACT TTGAGGGTTTCCCC AGTCTCCTCTCCTCCAGATTCCT 1594
     S   S  F  S  S  T  L   L  L  F  Q  S   S  P  E  S  A  Q  S  T  F  E  G  F  P  Q  S  P  L  Q  I  P   446

A1  ......................................................................................
C1  GTGAGCTCCTCCTCCTCCTA CACTTATTGAGTCTTTTTCC AGAGTTCCCCTGAGAGAACT CAGAGTACTTTTGAGGGTT TCCCCAGTCCCTCCTCCAGA 1694
     V  S  S  S  S  S   T  L   S  L  F  Q   S  S  P  E  R  T  Q  S  T  F  E  G  F  P  Q  S  P  L  Q  I   480

A1  ......................................................................................
C1  TTCCTGTGAGCTCCTCCTCC TCCTCCTCCTCCTCCACTT TATTGAG TCTTTTCCAGAGTTCCCCTG AGAGTGTACTCAAAGTACTTTT GAGGGTACTTT GAGGGTTTTCCCAGTCTCC 1794
     P  V  S  S  S  S   S  S  F  S  S  S   S  T  L  L  S  L  F  Q  S  S  P  E  C  T  Q  S  T  F  E  G  F  P  Q  S  P   513
```

```
A1  ..................................................................................................................   2794
C1  TGTGAGAGCTCCTTCCCCTCCT CCACTTCATCGAGTCTTTCC CAGAGTTCTCCTGTGAGCTC CTTCCCCTCCTCCACTTCAT CGAGTCTTTCCAAGAGTTCC    846
    V  S  S  F  P  S  S    T  S  S  S  L  S    Q  S  S  P  V  S  S    F  P  S  S  T  S  S    S  L  S  K  S  S

A1  ..................................................................   ---AGTGAAGGGTTCCAGCAG CCGTGAAGAGGAGGGGCCAA     89
C1  CCTGAGAGAGTCCCTCCAGAG TCCTGTGATCTCCTTCTCCT CCTCCACTTCATTGAGCCCA TTCAGTGAAGAGTCCAGCAG CCCAGTAGATGAATATACAA    468
    P  E  S  P  L  Q  S   P  V  I  S  F  S  S    S  T  S  L  S  P     S  S  E  E  S  S  S    P  V  D  E  Y  T  S    2894
                                                                                                                       880
                                                                                                                   S  E  G  S  S  S    R  E  E  E  G  P  S

A1  T  S  C  I  L  . . . . . . . . . . . . . . . . . . . . . .  ---GAGTCCTTGTTCCGAGCA GTAATCACTAAGAAGGTGGC      108
C1  GCACCTCTTGTATCCTG--- GAGAGTGATTCCTTGACAGA CAGCGAGTCCTTGATAGAGA GCCAGCCCTTGTTCACTTAT ACACTGGATGAAAAGGTGGA    523
    S  S  D  T  L  L      E  S  D  S  L  T  D    S  E  S  L  I  E  S   E  P  L  F  T  Y     T  L  D  E  K  V  D    2994
                                                                        E  S  L  F  R  A     V  I  T  K  K  V  A     913

A1  D  L  V  G  F  L  L    L  K  Y  R  A  R     E  P  V  T  K  A  E    M  L  E  S  V  I  K   N  Y  K  H  C  F     140
C1  TGATTTGGTTTGGTTTTCTGC TCCTCAAATATCGAGCCAGG GAGCCAGTCACAAAGGCAGA AATGCTGGAGAGTGTCATCA AAAATTACAAGCACTGTTTT    623
    C1 CGAGTTGGCGCGGTTCTTC TCCTCAAATATCAAGTGAAG CAGCCTATCACAAAGGCAGA GATGCTGACGAATGTCATCA GCAGGTACACGGGCTACTTT    3094
    E  L  A  R  F  L  L    L  K  Y  Q  V  K     Q  P  I  T  K  A  E    M  L  T  N  V  I  S   R  Y  T  G  Y  F     946

A1  P  E  I  F  G  K  A    S  E  S  L  Q  L  V   F  G  I  D  V  K      E  A  D  P  T  G  H   S  Y  V  L  V  T  C   174
C1  CCTGAGATCTTCGGCAAAGC CTCTGAGTCCTTGCAGCTGG TCTTTGGCATTGACGTGAAG GAAGCAGACCCCACCGGCCA CTCCTATGTCCTTGTCACCT    723
    CGAGTCTTCAGGAAAGC GGGTCTGAGTTGCTGAGTGA CCGTGTCTGAGTGATGAGCA GAAGTGGACCCT---GATGA CTCCTATGTCTTTGTAAACA    3191
    E  L  A  R  F  L  E  I  L    F  G  I  S  L  R    E  V  D  P  .  D  D    S  Y  V  F  V  N  T     979

A1  L  G  L  S  Y  D      G  L  L  G  D  N  Q    I  M  P  K  T  G  F   L  I  I  V  L  V      M  I  A  M  E  G  G   207
C1  GCCTAGGTCTCTCCTATGAT GGCCTGCTGGGTGATAATCA GATCATGCCCAAGACAGGCT TCCTGATAATTGTCCTGGTC ATGATTGCAATGGAGGGCGG   823
    CATTAGACCTCACCTCTGAG GGGTCTGAGTGTGCTGAGCA GGGCATGTCCCAGAACCGCC TCCTGATTCTTATTCTGAGT ATCATCTTCATAAAGGGCAC   3291
    L  D  L  T  S  E     G  C  L  S  D  E  Q     G  M  S  Q  N  R  L    L  L  I  L  S       I  I  F  I  K  G  T   1012

A1  H  A  P  E  E  E  I    W  E  E  L  S  F      M  E  V  Y  D  G  R   E  H  S  A  Y  G  E   P  R  K  L  L  T     240
C1  CCATGCTCCTGAGGAGGAAA TCTGGGAGGAGCTGAGTGTG ATGGAGGTGTATGATGGGAG GGAGCACAGTGCCTATGGGG AGCCCAGGAAGCTGCTCACC   923
    CTATGCCCTCTGAGGAGGTCA TCTGGGATGTCTGAGTGGA ATAGGGGTGCTGCTGGTGGA GGAGCACTTTGCCTTTGGGG AGCCCAGGGAGCTCCTCACT   3391
    Y  A  S  E  E  V  I    W  D  V  L  S  G      I  G  V  R  A  G  R   E  H  F  A  F  G  E   P  R  E  L  L  T     1045
```

FIG. 2(F)

```
        Q  D  L  V  Q  E  K     Y  L  E  Y  R  Q  V     P  D  S  D  P  A     R  Y  E  F  L  W  G     P  R  A  L  A  E  T   274
A1 CAAGATTTGGTGCAGGAAAA GTACCTGGAGTACCGGCAGGT TGCCGGACAGTGATCCCGCA CGCTATGAGTTCCTGTGGGG TCCAAGGGCCCTCGCTGAAA 1023
C1 AAAGTTTGGGTGCAGGAACA TTACCTAGAGTACCGGGAGG TGCCCAACTCTTCCTCCT CGTTACGAATTCCTGTGGGG TCCAAGAGCTCATTCAGAAG 3491
         K  V  W  V  Q  E  H     Y  L  E  Y  R  E  V     P  N  S  S  P  P     R  Y  E  F  L  W  G     P  R  A  H  S  E  V  1079

S  Y  V  K  V  L        E  Y  V  I  K  V  S     A  R  V  R  F  F  F     P  S  L  R  E  A       A  L  R  E  E  E  E   307
A1 CCAGCTATGTGAAAGTCCTT GAGTATGTGATCAAGGTCAG TGCAAGAGTTCGCTTTTCT TCCCATCCCTGCCTGAAGCA GCTTTGAGAGAGGAGGAAGA 1123
C1 TCATTAAGAGGAAAGTAGTA GAGTTTTTGGCCATGCTAAA GAATACCGTCCCTATTACCT TTCCATCCTCTTACAAGGAT GCTTTGAAAGATGTGGAAGA 3591
         I  K  R  K  V  V        E  F  L  A  M  L  K      N  T  V  P  I  T  F     P  S  S  Y  K  D       A  L  K  D  V  E  E  1112

G  V  OPA                                                                                                                309
A1 GGGAGTCTGAGCATGAGTG CAGCCAAGGCCAGTGGGAGG GGGACTGGGCCAGTGCACCT TCCAGGGCCGCGGTCCAGCAG CTTCCCCTGCCTCGTGTGAC 1223
C1 GAGAGCCAGGCCAGTCGACT ACACCAGATGATTCGACT GCCACAGAAAGTGCAAGCTC CAGTGTCATGTCCCCCAGCT TCTCTTGAGTGAAGTCATA 3691
         R  A  Q  A  I  I  D       T  D  D  S  T          A  T  E  S  A  S  S      S  V  M  S  P  S  F      S  S  E   OPA       1142

A1 ---ATGAGGCCCATTCTTCA CTCTGAAGAGAGCGGTCAGT GTTCTCAGTAGTAG------ ------------------GTTTC 1279
C1 GGGCAGATTCTTCCCCTCTGA GTTGAAGGGGGGCAGTCGAG TTTGAGGCTGGAGAGAAC ACAGTGCTATTTGCATTTCT 3791

A1 TGTTCTATTGGGTGACTTGG AGATTATCTTTGTTCTCTT TTGGAATTGTTCAAATGTTT TT--TTTAAGGGATGGTTG AATGAACTTCAGCATCCAAG 1377
C1 GTTCCATATGGGTAGTTATG GGGTTTACCTGTTTTACTTT TGGGTATTTTCAAATGCTT TTCCTATTAATAACAGGTTT AAATAGCTTCAGAATCCTAG 3891

A1 TTTATGAATGACAGCAGT-C ACACAGTTCTGTGTATATAG TTTAAGGGTAAGAGTCTTGT GTTTTATTCAGATTGGGAAA TCCATTCTATTTTGTGAATT 1476
C1 TTTATGCACATGAGTCGCAC ATGTATTGCTGTTTTCTGG TTTAAGAGTAACAGTTTGAT ATTTTGTAAAAACAAAAACA CACCCAAACACACCACATTG 3991

A1 GGGATAATAACAGCAGTGGA ATAAGTACTTAGAGAATGTGA AAAATGAGCAGTAAAATAGA TGAGATAAAGAACTAAAGAA ATTAAGAGATAGTCAATTCT 1576
C1 GGAAAACCTTCTGCCTCATT TTGTGATGTGTCACAGGTTA ATGTGGTGTTACTGTAGGAA TTTCTTGAAACTGTGAAGG AACTCTGCAGTTAAATAGTG 4091

A1 TGCCTTATACCTCAGTCTAT TCTGTAAAATTTTTAAAGAT ATATGCATACCTGGATTCC TTGGCTTCTTTGAGAATGTA AGAGAAATTAAATCTGAATA 1676
C1 GAATAAAGTAAAGGATTGTT AATGTTTGCATTTCCTCAGG TCCTTTAGTCTGTGTTGTCTT GAAAACTAAAGATACATACC TGGTTTGCTTGGCTTACGTA 4191

A1 AAGAATTCTTCCTGT---- ...........          1691
C1 AGAAAGTAGAAGAAAGTAAA CTGTAATAAATAAA        4225
```

ISOLATED NUCLEIC ACID MOLECULE CODING FOR TUMOR REJECTION ANTIGEN PRECURSORS MAGE-C1 AND MAGE-C2 AND USES THEREOF

RELATED APPLICATION

This application is a divisional application of U.S. application Ser. No. 09/066,281 having a filing date of Apr. 24, 1998 now U.S. Pat. No. 6,475,783, which is a continuation-in-part of Ser. No. 08/845,528 filed on Apr. 25, 1997, now U.S. Pat. No. 6,027,924 incorporated by reference.

FIELD OF THE INVENTION

This invention relates to a nucleic acid molecules which code for tumor rejection antigen precursors. More particularly, the invention concerns nucleic acid molecules which encode tumor rejection antigen precursors which can be processed, inter alia, into peptides presented by many MHC molecules, such as HLA-A1 and its alleles, HLA-A2, HLA-Cw*1601, HLA-B44, and so forth. MAGE-C1, a preferred embodiment, shares partial homology with other members of the MAGE family known to date but is approximately 2 kb larger. MAGE-C2 is another preferred embodiment. These nucleic acid molecules are expressed in a variety of tumors and in normal testis cells, but are not expressed by other normal cells.

BACKGROUND AND PRIOR ART

The process by which the mammalian immune system recognizes and reacts to foreign or alien materials is a complex one. An important facet of the system is the T lymphocyte, or "T cell" response. This response requires that T cells recognize and interact with complexes of cell surface molecules, referred to as human leukocyte antigens ("HLA"), or major histocompatibility complexes ("MHCs"), and peptides. The peptides are derived from larger molecules which are processed by the cells which also present the HLA/MHC molecule. See in this regard Male et al., *Advanced Immunology* (J. P. Lipincott Company, 1987), especially chapters 6–10. The interaction of T cells and HLA/peptide complexes is restricted, requiring a T cell specific for a particular combination of an HLA molecule and a peptide. If a specific T cell is not present, there is no T cell response even if its partner complex is present. Similarly, there is no response if the specific complex is absent, but the T cell is present. This mechanism is involved in the immune system's response to foreign materials, in autoimmune pathologies, and in responses to cellular abnormalities. Much work has focused on the mechanisms by which proteins are processed into the HLA binding peptides. See in this regard, Barinaga, *Science* 257:880 (1992); Fremont et al., *Science* 257:919 (1992); Matsumura et al., *Science* 257:927 (1992); Latron et al., *Science* 257:964 (1992).

The mechanism by which T cells recognize cellular abnormalities has also been implicated in cancer. For example, in PCT application PCT/US92/04354, filed May 22, 1992, published on Nov. 26, 1992, and incorporated by reference, a family of genes is disclosed, which are processed into peptides which, in turn, are expressed on cell surfaces, which can lead to lysis of the tumor cells by specific cytolytic T lymphocytes ("CTLs"). The genes are said to code for "tumor rejection antigen precursors" or "TRAP" molecules, and the peptides derived therefrom are referred to as "tumor rejection antigens" or "TRAs." See Traversari et al., *Immunogenetics* 35:145 (1992); van der Bruggen et al., *Science* 254:1643 (1991), for further information on this family of genes. Also, see U.S. Pat. No. 5,342,774 and U.S. Pat. No. 5,462,871 incorporated by reference in their entirety.

In U.S. Pat. No. 5,405,940 the disclosure of which is incorporated by reference, it is explained that the MAGE-1 gene codes for a tumor rejection antigen precursor, which is processed to nonapeptides which are presented by the HLA-A1 molecule. The nonapeptides which bind to HLA-A1 follow a "rule" for binding in that a motif is satisfied. In this regard, see, e.g., PCT/US93/07421; Falk et al., *Nature* 351:290–296 (1991); Engelhard, *Ann Rev. Immunol.* 12:181–207 (1994); Ruppert et al., *Cell* 74:929–937 (1993); Rötzschke et al., *Nature* 348:252–254 (1990); Bjorkman et al., *Nature* 329:512–518 (1987); Traversari et al., *J. Exp. Med.* 176:1453–1457 (1992). The reference teaches that given the known specificity of particular peptides for particular HLA molecules, one should expect a particular peptide to bind to one HLA molecule, but not to others. Because different individuals possess different HLA phenotypes, identification of a particular peptide as being a partner for a particular HLA molecule has diagnostic and therapeutic ramifications, only for individuals with that particular HLA phenotype. There is a need for further work in the area, because cellular abnormalities are not restricted to one particular HLA phenotype, and targeted therapy requires some knowledge of the phenotype of the abnormal cells at issue.

In U.S. patent application Ser. No. 288,977, filed Aug. 11, 1994 now U.S. Pat. No. 5,629,166 and incorporated by reference, the fact that the MAGE-1 expression product is processed to a second TRA is disclosed. This second TRA is presented by HLA-Cw*1601 molecules. The disclosure shows that a given TRAP can yield a plurality of TRAs, each of which will satisfy a motif rule for binding to an MHC molecule.

In U.S. patent application Ser. No. 994,928, filed Dec. 22, 1992, and incorporated by reference herein teaches that tyrosinase, a molecule which is produced by some normal cells (e.g., melanocytes), is processed in tumor cells to yield peptides presented by HLA-A2 molecules.

In U.S. patent application Ser. No. 08/032,978, filed Mar. 18, 1993, and incorporated by reference in its entirety, a second TRA, not derived from tyrosinase is taught to be presented by HLA-A2 molecules. The TRA is derived from a TRAP, but is coded for by a non-MAGE gene. This disclosure shows that a particular HLA molecule may present TRAs derived from different sources.

In U.S. patent application Ser. No. 08/079,110, filed Jun. 17, 1993 now U.S. Pat. No. 5,571,711 issued Jan. 5, 1996 and incorporated by reference herein, an unrelated tumor rejection antigen precursor, the so-called "BAGE" precursor is described. The BAGE precursor is not related to the MAGE family.

In U.S. patent application Ser. No. 08/096,039 and Ser. No. 08/250,162, both of which are incorporated by reference, a non-MAGE TRAP precursor, GAGE, is also disclosed.

U.S. application Ser. No. 08/316,231 filed Sep. 30, 1994, discloses that additional tumor rejection antigen precursors. These tumor rejection antigen precursors are referred to as "DAGE" tumor rejection antigen precursors. They do not show homology to the MAGE, the BAGE, or GAGE family of genes.

The work which is presented by the papers, patent, and patent applications cited supra deals, in large part, with the MAGE, BAGE, GAGE, and DAGE family of genes. The present invention relates to nucleic acid molecules encoding a MAGE-related tumor rejection antigen precursor, i.e., MAGE-C1 and MAGE-C2, and to the tumor rejection antigen precursors and tumor rejection antigens themselves. The invention also relates to applications of both nucleic acid and protein molecules.

The invention is elaborated upon further in the disclosure which follows.

BRIEF DESCRIPTION OF THE FIGURES

FIG. 1 is the nucleotide sequence of MAGE-C1 cDNA (SEQ ID NO: 1). The position of various nucleotide sense and antisense primers are indicated.

FIG. 2, depicts a comparison of the nucleotide sequences of MAGE-C1 and MAGE-A1 (SEQ ID NO: 9 and SEQ ID NO: 8).

DETAILED DESCRIPTION

Figure 3:
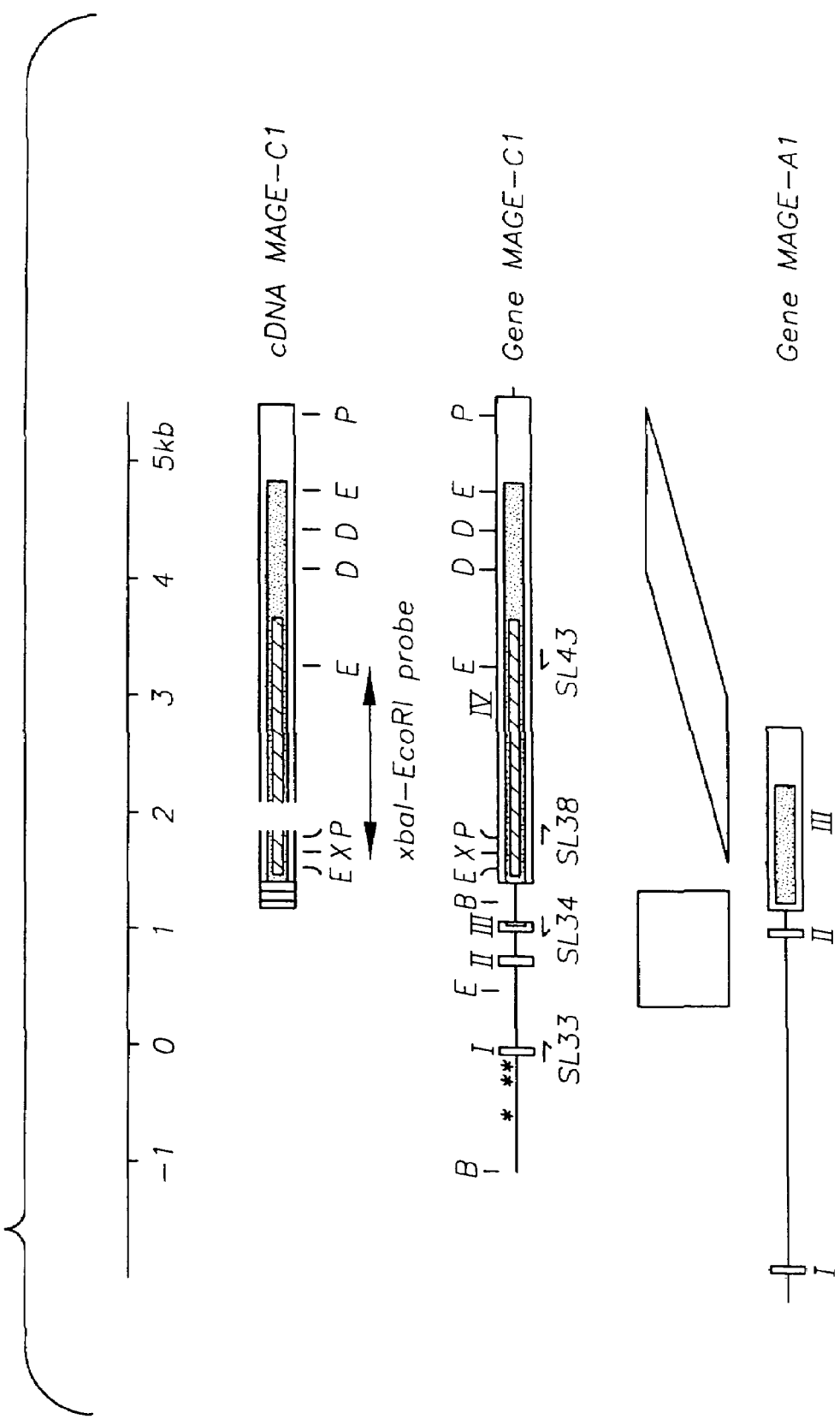
FIG. 3 is a comparison of gene MAGE-C1 with isolated cDNA clone MAGE-C1 and published gene MAGE-A1. Exons appear as boxes and are numbered from 1 to 111 (MAGE-A1) or IV (MAGE-C1). Introns appear as lines. Deletion in the cDNA clone as compared to gene MAGE-C1 appears as a blank. Similar regions between genes MAGE-A1 and MAGE-C1 are indicated by shaded areas. Open reading frames are indicated by dark boxes inside the exons. Repeated segments in gene MAGE-C1 are shown as a hatched box, important restriction sites are indicated (B: BamHI, D: Dpnll, E: EcoRI, P: PstI, X: XbaI), as well as positions of two pairs of oligonucleotides (SL33/SL34, and SL38/SL43). Asterix upstream from MAGE-C1 exon I show localization of the Sp1 and the 2 Ets consensus recognition sequences. The position of the XbaI-EcoRI cDNA probe is also indicated.

Many human tumor antigens identified so far are encoded by genes, such as MAGE, BAGE, and GAGE, which share a common expression pattern: they are expressed in testis (and sometimes placenta), but in no other normal tissue, and are reactivated in various tumor types. This type of antigen is of particular interest for tumor immunotherapy.

As an alternative to the identification of tumor antigens by cloning genes coding for antigens known to be recognized by antitumor cytolytic T lymphocytes (CTL), we searched directly for new genes expressed specifically in tumors, as such genes could provide a source of tumor-specific antigens. Using a PCR based subtractive hybridization technique called Representational Difference Analysis applied to cDNA (Hubank and Shatz, "Identifying Differences in mRNA Expression By Representational Difference Analysis of cDNA," *Nucleic Acids Res.* 22:5640–5648 (1994)), we identified new members of the MAGE gene family, which we describe herein.

The examples of this invention show the isolation of nucleic acid molecules which code for tumor rejection antigen precursors ("TRAP"), MAGE-C1 and MAGE-C2. These TRAP encoding molecules share partial homology with the MAGE family coding sequences described in the references set forth supra. Hence, one aspect of the invention is an isolated nucleic acid molecule which encodes a protein having the amino acid sequence encoded by the nucleotide sequence set forth in SEQ ID NO: 9 and an isolated nucleic acid molecule which encodes a protein having the amino acid sequence encoded by the nucleotide sequence set forth in SEQ ID NO: 18. Preferably, the nucleic acid molecule is a cDNA molecule. SEQ ID NO: 9 and SEQ ID NO: 18 are not previously known MAGE, BAGE, or GAGE coding sequences, as will be seen by comparing it to the sequence of any of these genes as described in the cited references.

Figure 2D:
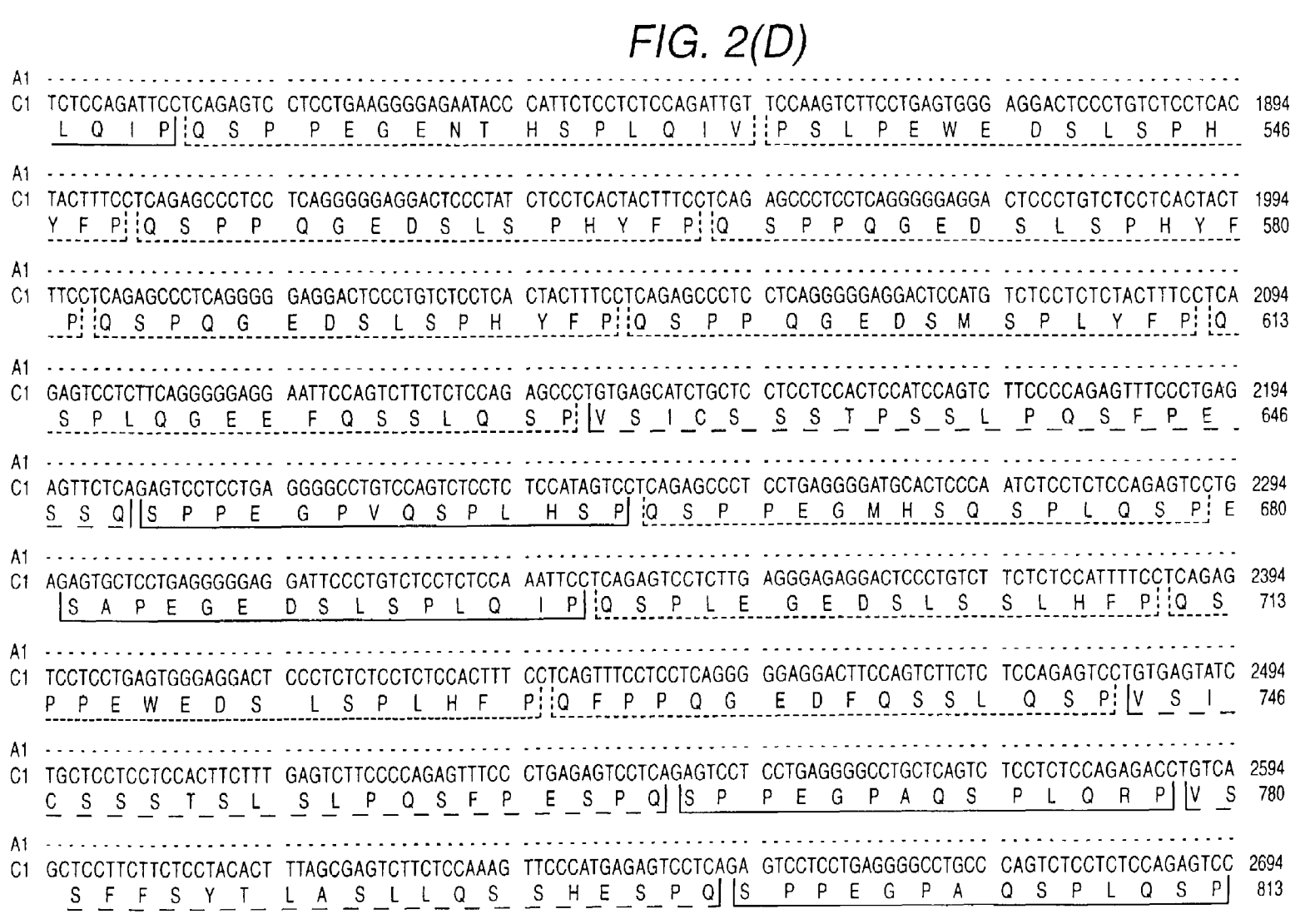

Also, a part of the invention are those nucleic acid molecules having the nucleotide sequence of nt 1–2815 and nt 2816–4225 of SEQ ID NO: 9. Another embodiment of this invention is a nucleic acid molecule, which codes for a tumor rejection antigen precursor and hybridizes to a nucleic acid molecule having the nucleotide sequence 1–2815 of SEQ ID NO: 9 but does not hybridize to nucleic acid molecules having the nucleotide sequence of SEQ ID NO: 8, i.e., the MAGE-A1 nucleotide sequence as set forth in FIG. 2, under stringent conditions. A further embodiment of this invention is a nucleic acid molecule which codes for a tumor rejection antigen precursor and hybridizes to a nucleic acid molecule having the nucleotide sequence 261–2856 of SEQ ID NO: 9 but does not hybridize to nucleic acid molecules having the nucleotide sequence of SEQ ID NO: 8. The term "stringent conditions" as used herein, refers to hybridization in 5×SSC, 0.1% SDS, 5× Denhardt's reagent at 65° C., overnight, followed by two washes at room temperature for 20 minutes, in 2×SSC and 0.1% SDS, and one wash for 20 minutes in 2×SSC and 0.1% SDS at 65° C., and one wash in 0.2×SSC, 0.1% SDS at 65° C. There are other conditions, reagents, and so forth which can be used, which result in the same or higher degree of stringency. The skilled artisan will be familiar with such conditions and, thus, they are not given here.

The widespread distribution in the expression of MAGE-C1 and MAGE-C2 in tumor cells and not in normal cells, demonstrates that the isolated nucleic acid molecule can be used as diagnostic probes to determine the presence of abnormal, e.g., tumor, cells which express MAGE-C1 or MAGE-C2 related sequences. The identification of seminoma with MAGE-C1 was 100% (Table 2) so on a very basic level, the isolated nucleic acid molecules may be used to determine whether or not seminoma is present. Note, that there are many ways available to the skilled artisan to confirm that a tumor sample is a seminoma, and these need not be reiterated here.

It will also be seen from the examples that the invention embraces the use of the sequences in expression vectors, which may be used to transform or to transfect host cells and cell lines, be these prokaryotic (e.g., *E. coli*), or eukaryotic (e.g., CHO or COS cells). The expression vectors require that the pertinent sequence, i.e., those described supra, be operably linked to a promoter. The expression vector may include, e.g., a sequence encoding one or more HLA molecules. In a situation where the vector contains both coding sequences, it can be used to transform or transfect a cell which does not normally express either one. The tumor rejection antigen precursor coding sequence may be used alone, when, e.g., the host cell already expresses HLA-molecules. The particular host cell which is suitable for expressing the sequences described herein include, e.g., prokaryotic or eukaryotic cells, such as *E. coli*, CHO, COS cells or insect cells.

Another aspect of this invention is the isolation of a genomic DNA (gDNA) which encodes a protein having the amino acid sequence encoded by a nucleic acid molecule having SEQ ID NO: 9 or SEQ ID NO: 18. Such a gDNA may be identified and isolated using well-known methods in the art. For example MAGE-C1 specific probes derived from SEQ ID NO: 9 or MAGE-C2 specific probes derived from SEQ ID NO: 18 may be used to screen a genomic DNA library prepared from, e.g., LB373-MEL cells. Those of ordinary skill in the art will be able to determine from sequence analysis those sequences which are specific for MAGE-C1 and/or MAGE-C2. It is also possible using techniques well known in the art to determine the chromosome where such a gDNA is located, see, e.g., PCT/US95/02203 incorporated in its entirety by reference.

Another embodiment of this invention is an expression kit, which enables the artisan to prepare a desired expression vector or vectors. Such expression kits include at least separate portions of each of the previously discussed coding sequences, e.g., a vector such as a bacterial plasmid, a cosmid or a viral vector which comprises a promoter (De-Plaen et al., *Proc. Natl. Acad. Sci.* 85:2274–2278 (1988), Grosveld et al., *Gene* 10:6715–6732 (1982), and Bates et al., *Gene* 26:137–146 (1983) incorporated in their entirety by reference, any of the HLA coding sequences, such as those set forth in Zemmour and Parham, *Immunogenetics* 37:239–250 (1993), a MAGE-C1 or MAGE-C2 coding sequence, or both an HLA and a MAGE-C1 or MAGE-C2 coding sequence. Other components, such as, e.g., resistance markers, enhancers or inducible promoters which are known in the art may be added, as desired.

To distinguish the nucleic acid molecules and the TRAPs and TRAs of this invention from the previously described MAGE, BAGE, and GAGE materials, the invention shall be referred to as the MAGE-C1 gene, MAGE-C2 gene, MAGE-C1 TRAP and TRAs and MAGE-C2 TRAP and TRAs. Hence, whenever MAGE-C1 or MAGE-C2 is used herein, it refers to the tumor rejection antigen precursors, and their derived TRAs, which are encoded for by the previously unknown nucleic acid sequences. "MAGE-C1 coding sequence," "MAGE-C2 coding sequence" and similar terms, are used to describe the nucleic acid molecules themselves.

The invention as described herein has a number of uses, some of which are described herein. First, the invention permits the artisan to diagnose a disorder characterized by expression of the MAGE-C1 or MAGE-C2 messenger RNAs and the MAGE-C1 or MAGE-C2 TRAPs and TRAs. The methods involve determining the expression of mRNAs from the MAGE-C1 and MAGE-C2 nucleic acid molecules and related molecules, and/or the presence of TRAs derived from the TRAP encoded by MAGE-C1 or MAGE-C2 and related nucleic acid molecules. In the former situation, such determinations can be carried out via any standard nucleic acid determination assay, including the polymerase chain reaction, or assaying with labeled hybridization probes. In the latter situation, TRAP and TRA may be detected by assaying for the TRAP or TRA alone or assaying for complexes of TRA and HLA, using binding partners such as, e.g., as antibodies. Another embodiment of this invention is to detect the presence of cytolytic T cells specific for complexes of an HLA molecule and a peptide derived from the protein encoded by the isolated nucleic acid molecule of claim 1 in a CTL-containing sample, comprising contacting-said sample with cells, which present said complexes on their surface, and determining (I) proliferation of cytolytic T cells, or (ii) lysis of cells presenting said complexes, as a determination of said cytolytic T cells in said sample. CTL proliferation may be detected by assaying TNF release or the release of a radiolabelled substance, such as $^{51}Cr$, as described, e.g., in PCT/US95/02203 incorporated in its entirety by reference. In addition, CTL may be detected by ELISPOT analysis as per Schmitt et al., *J. Immunol. Meth.*, 210:167–179 (1997) and Lalvani et al. *J. Exp. Med.*, 186:859 (1997), both of which are incorporated by reference or by FACS analysis of fluorogenic tetramer complexes of MHC class I/peptide (Dunbar et al. *Current Biology*, 8:713–716 (1998)).

The isolation of these MAGE-C1 and MAGE-C2 nucleic acid molecules also makes it possible to isolate the TRAP molecules themselves, especially TRAP molecules consisting of the amino acid sequence encoded by SEQ ID NO: 9 or SEQ ID NO: 18. The isolation of the MAGE-C1 and MAGE-C2 nucleic acid molecules also makes it possible to identify TRAs that are unique to MAGE-C1 or MAGE-C2 discussed in more detail infra.

Further, the polypeptide having the amino acid sequence encoded by nucleotide sequence 257–3682 of SEQ ID NO: 9, the polypeptide having the amino acid sequence encoded by nucleotide sequence 330–1449 of SEQ ID NO: 18 and polypeptides derived therefrom are also part of this invention. These polypeptides alone or in combination with other polypeptides from other TRAP molecules, for example, may be combined with materials such as adjuvants which are well-known in the art see, e.g., U.S. Pat. No. 5,057,540 to Kensil et al., incorporated by reference or PCT application PCT/US92/03579 to Scott et al., also incorporated by reference to produce vaccines which will be useful in treating disorders characterized by expression of the molecules.

Peptides derived from the polypeptide having the amino acid sequence encoded by nucleotide sequence 257–3682 of SEQ ID NO: 9 and the polypeptide having the amino acids sequence encoded by nucleotide sequence 330–1449 of SEQ ID NO: 18 which are presented by MHC molecules and recognized by CTL may be combined with peptide from other tumor rejection antigens to form "polytopes." Exemplary peptides include those listed in U.S. patent application Ser. Nos. 08/672,351, 08/718,964 now U.S. Pat. No. 5,932,694; Ser. No. 08/487,135 now U.S. Pat. No. 5,821,122, Ser. No. 08/530,569, now U.S. Pat. No. 5,939,526 and Ser. No. 08/880,963, now U.S. Pat. No. 6,025,470, all of which are incorporated by reference.

Additional peptides which can be used are those described in the following references, all of which are incorporated by reference: U.S. Pat. Nos. 5,405,940; 5,487,974; 5,519,117; 5,530,096; 5,554,506; 5,554,724; 5,558,995; 5,585,461; 5,589,334; 5,648,226; and 5,683,886, PCT International Publication Nos. 92/20356; 94/20356; 96/10577; 96/21673; 97/10837; 97/26535; and 97/31017, as well as pending U.S. application Ser. No. 08/713,354.

Polytopes are groups of 2 or more potentially immunogenic or immune stimulating peptides, which can be joined together in various ways, to determine if this type of molecule will stimulate and/or provoke an immune response.

These peptides can be joined together directly, or via the use of flanking sequences. See Thomson et al., *Proc. Natl. Acad. Sci. USA*, 92(13):5845–5849 (1995) (incorporated by reference), teaching the direct linkage of relevant epitopic sequences. The use of polytopes as vaccines is well known. See, e.g., Gilbert et al., *Nat. Biotechnol.*, 15(12):1280–1284 (1997): Thomson et al., supra; Thomson et al., *J. Immunol.*, 157(2):822–826 (1996); Tam et al., *J. Exp. Med.*, 171(1):299–306 (1990), all of which are incorporated by reference.

Tam et al., in particular, shows that polytopes, when used in a mouse model, are useful in generating both antibody and protective immunity. Further, the reference shows that the polytopes, when digested, yield peptides which can be and are presented by MHCs. Tam et al. shows this by demonstrating recognition of individual epitopes processed from polytope "strings," via CTLs. This approach can be used, e.g., in determining how many epitopes can be joined in a polytope, and still provoke recognition and also to determine the efficacy of different combinations of epitopes. Different combinations may be "tailor-made" for patients expressing particular subsets of tumor rejection antigens. These polytopes can be introduced as polypeptide structures, or via the use of nucleic acid delivery systems. To elaborate, the art has many different ways available to introduce DNA encoding an individual epitope, or a polytope such as is discussed supra. See, e.g., Allsopp et al., *Eur. J. Immunol.* 26(8): 1951–1959 (1996), incorporated by reference. Adenovirus, pox virus, Ty-virus like particles, plasmids, bacteria, etc., can be used. One can test these systems in mouse models to determine which system seems most appropriate for a given, parallel situation in humans. They can also be tested in human clinical trials.

In addition, vaccines can be prepared from cells, such as non-proliferative cancer cells, non-proliferative transfectants, etcetera, which present the TRA/HLA complexes on their surface. In all cases where cells are used as a vaccine, the cells may be transfectants having been transfected with coding sequences for one or both of the components necessary to provide a CTL response, i.e., TRAP, TRA, and HLA molecules using techniques which are well-known in the art see, e.g., PCT/US95/02203 and Zemmour supra for sequence of various HLA molecules. Alternatively, the cells may express both HLA and TRAP/TRA molecules without transfection. Further, the TRAP molecules, their associated TRAs, as well as complexes of TRA and HLA, may be used to produce antibodies, using standard techniques well known in the art.

When "disorder" is used herein, it refers to any pathological condition where the tumor rejection antigen precursor is expressed. An example of such a disorder is cancer, seminoma in particular.

Therapeutic approaches based upon the disclosure herein are premised on a response by a subject's immune system, leading to lysis of HLA/TRA presenting cells. One such approach is the administration of CTLs which are specific to an HLA/TRA complex to a subject having abnormal cells of the phenotype at issue. It is within the skill of the artisan to develop such CTLs in vitro see, e.g., Herin et al. supra. For example, a sample of cells, such as blood cells, are contacted to a target cell presenting an HLA/TRA complex and capable of provoking a specific CTL to proliferate. The target cell can be a transfectant, such as a COS cell transfected with and expressing a particular HLA and TRAP as described supra. These transfectants present the desired complex on their surface and, when combined with a CTL of interest, stimulate its proliferation. COS cells, such as those used herein are widely available, as are other suitable host cells including but not being limited to, CHO cells, *Spodopitera furjiperda, E. Coli, Bacillus,* and so forth.

One therapeutic methodology is referred to as adoptive transfer (Greenberg, *J. Immunol.* 136(5): 1917 (1986); Riddel et al., *Science* 257: 238 (Jul. 10, 1992); Lynch et al., *Eur. J. Immunol.* 21: 1403–1410 (1991); Kast et al., *Cell* 59: 603–614 (Nov. 17, 1989)). In adoptive transfer, cells presenting the desired HLA/TRA complex are combined with CTLs leading to proliferation of the CTLs which are specific for that complex. The proliferated CTLs are then administered to a subject with a cellular abnormality which is characterized by certain of the abnormal cells presenting the particular complex. The CTLs then lyse the abnormal cells, thereby achieving the desired therapeutic goal.

The foregoing therapy assumes that at least some of the subject's abnormal cells present the relevant HLA/TRA complex. This can be determined easily, as the art is very familiar with methods for identifying cells which present a particular HLA molecule, as well as how to identify cells expressing DNA of the pertinent sequences, in this case a MAGE-C1 or a MAGE-C2 and related sequences. If the abnormal cells of the patient present the relevant HLA/TRA complex then the patient is an appropriate candidate for the therapeutic approaches set forth supra.

Adoptive transfer is not the only form of therapy that is available in accordance with the invention. CTLs can also be provoked in vivo, using a number of approaches. One approach, i.e., the use of non-proliferative cells expressing the complex as a vaccine, has been elaborated upon supra. The cells used in this approach may be those that normally express the complex, such as irradiated seminoma cells or irradiated cells transfected with one or both of the genes necessary for presentation of the complex. Chen et al., *Proc. Natl. Acad. Sci. USA* 88:110–114 (January 1991) exemplifies this approach, showing the use of transfected cells expressing HPV E7 peptides in a therapeutic regime. Various cell types may be used.

Similarly, vectors, such as viral or bacterial vectors, carrying a nucleic acid molecule encoding either an HLA or a TRAP or TRA, or combination thereof, may be used. In these systems, the nucleic acid molecule is carried by, e.g., a Vaccinia virus or the bacteria BCG, which "infect" host cells. The infected cells present the HLA/TRA complex and are recognized by autologous CTLs, which then proliferate.

CTLs can also be provoked in vivo by combining the TRA or the TRAP itself with an adjuvant to facilitate incorporation into HLA presenting cells. The cells present the HLA/peptide complex of interest by further processing the TRAP to yield the peptide partner of the HLA molecule. Alternatively, the cells may present the TRA without the need for further processing. See, e.g., Braciale, T. J. and Braciale, V. L., *Immunology Today* 12:124–129 (1991); T. Elliot, *Immunology Today* 12:386–388 (1991), and: Madelboim et al., *Nature* 369:67–71(1994).

Also, a feature of this invention are isolated peptides derived from the MAGE-C1 TRAP or MAGE-C2 TRAP, which conform to the rules for presentation by MHC molecules. For example, in PCT application No. PCT/US93/07421, incorporated by reference herein, several motifs are described as being associated with different MHC molecules. These motifs, incorporated by reference herein, as well as those taught by, e.g., Falk et al., *Nature* 351:290–296 (1991); Engelhard, *Ann. Rev. Immunol* 12:181–207 (1994); Ruppert et al., *Cell* 74:929–937 (1993); Rötzschke et al., *Nature* 348:252–254 (1990); Bjorkman et al., *Nature* 329: 512–518 (1987) and Traversari et al., *J. Exp. Med.* 176: 1453–1457 (1992) all of which are incorporated by reference, serve as a basis for identifying appropriate peptides obtainable or derivable from the MAGE-C1 amino acid sequence and the nucleotide sequence which encodes the protein. In another aspect of the invention these peptides may be used alone, or in mixtures, to stimulate CTL proliferation. These peptides are also useful in vaccines.

It is well established that the blood of individuals afflicted with tumors frequently contains cytolytic T cells ("CTLs") which recognize complexes of MHC molecules and presented peptides. See, e.g., Robbins et al., *Canc. Res.* 54:3124–3126 (1994); Topolian et al., *J. Immunol.* 142: 3714–3725 (1989); Coulie et al., *Int. J. Cancer* 50:289–297 (1992), all of which are incorporated by reference. Also, note Kawakami et al., *J. Exp. Med.* 180:347–352 (1994); Hom et al., *J. Immunother.* 10:153–164 (1991), Darrow et al, *J. Immunol.* 142(9):3329–3335 (1989); Slovin et al., *J. Immunol.* 137(9):3042–3048 (1986), all of which are incorporated by reference. These papers all establish the usefulness of a CTL proliferation assay to diagnose possible cancer.

In general, a patient will only have CTLs which recognize and proliferate in response to contacting target cells presenting particular complexes of TRA and HLA only if at least some of the patient's own cells are also expressing that particular complex. If one takes a peripheral blood lymphocyte (PBL) containing sample from a patient suspected of having abnormal cells, e.g., tumor cells, and contacts that CTL-containing sample with a target cell which presents complexes of a relevant MHC molecule and a MAGE-C1 or a MAGE-C2 derived peptide one will only see proliferation of CTLs which are specific for that complex. Thus proliferation of CTLs in the patient's PBL sample will indicate that the patient possibly has tumor cells which express that particular HLA/TRA complex. The target cells may be cells which normally present the MHC molecule in question or may be cells which have been transfected with an HLA coding sequence. The target cells may conceivably be tumor cells, or normal cells.

One embodiment of the invention involves mixing a target cell sample with (1) a peptide or mix of peptides which are derived from a MAGE-C1 TRAP or a MAGE-C2 TRAP and presented by the target cell MHC molecules and (2) a PBL sample of the subject under evaluation. The mixture is then tested for CTL proliferation. Various methods of determining CTL proliferation are known in the art, e.g., TNF release assays, and $^{51}$Cr release assays see, e.g., PCT/US95/02203.

The peptide or peptides of this invention may also be combined with one or more adjuvants to stimulate a more pronounced CTL response. Exemplary of such adjuvants are saponins and their derivatives, such as those disclosed by U.S. Pat. No. 5,057,540 to Kensil et al., incorporated by reference or PCT application PCT/US92/03579 to Scott et al., also incorporated by reference. Of course, standard adjuvants, such as Freund's complete adjuvant, or Freund's incomplete adjuvant, may also be used.

Other aspects of the invention will be clear to the skilled artisan and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

EXAMPLE 1

Generation of Difference Products (DP) for Tumor LB373-MEL and Testis

A cDNA library enriched for sequences present only in the cell type of interest, a "tester" cell, and not present in another cell type, a "driver" cell, was generated essentially as described by Hubank and Schatz, *Nucl. Acids. Res.* 22:5640–5648 (1994) incorporated herein in its entirety by reference. Briefly, total RNA was prepared from tester cells and driver cells. Herein the tester cells were melanoma cells LB373-MEL and the driver cells were normal skin cells. Poly-A+ RNA was isolated from total RNA using oligo-dT columns using techniques well known in the art. The poly-A+ RNA was then reverse transcribed to produce cDNA. The cDNA was digested with restriction enzyme Dpnll, which cuts DNA at GATC sites, to generate short fragments of double stranded DNA with 5'-GATC overhangs. Double-stranded DNA adapters with a 5'-GATC overhangs (R-Bgl adaptor which is composed of annealed R-Bgl-12 and R-Bgl 24 oligonucleotide SEQ ID NO: 2 and SEQ ID NO: 11 respectively) were ligated to the Dpnll digested cDNA prepared from the tester and driver cells. The adaptor-ligated cDNA was subsequently amplified by the well-known polymerase chain reaction (PCR). The amplified product is a "representation" of the tester and the driver, respectively. Both tester and driver representations were digested with Dpnll. Digested tester was ligated to new adaptor molecules (J-Bgl adaptor which is composed of annealed J-Bgl-12 and J-Bgl-24 oligonucleotide SEQ ID NO: 3 and SEQ ID NO: 12 respectively). A first round of subtractive hybridization was then performed by mixing in 100/1 proportions the digested driver cDNA with the digested tester cDNA ligated to the J-Bgl adapters. The mixed driver and tester cDNA sample was denatured at 98° C. for 5 min and then incubated at 67° C. for 20 hours to rehybridize the denatured sample. This resulted in a mixture of hybrid double-stranded cDNAs. The hybrid cDNAs were of three types. One hybrid type constituted two tester cDNA molecules which represented nucleotide sequences unique to the tester cells, a second hybrid type constituted two driver cDNA molecules and a third hybrid type constituted one tester cDNA molecule and one driver cDNA molecule. After hybridization, the sample was PCR amplified using a single stranded J-Bgl adaptor, J-Bgl-24 SEQ ID NO: 12. Hybrid cDNAs composed of two driver cDNA molecules were not amplified, because they did not comprise the J-Bgl adaptor. Hybrid cDNAs constituted by one tester cDNA molecule and one driver cDNA molecule were only amplified linearly. Only double stranded cDNA consisting of two tester cDNA molecules were amplified exponentially.

After 10 cycles of PCR amplification as described supra, the sample was treated with Mung Bean Nuclease (which digests specifically the single stranded DNA produced by the linear amplification), then subjected to 18 additional PCR cycles. The resulting enriched product was designated difference product 1 (DP1). DP1-Testis [-HLLK] and DP1-LB373 [-skin] were both generated.

J-Bgl adapters on DP1 were changed for N-Bgl-12/24 adapters (N-Bgl-12: 5'GATCTTCCCTCG-3'; N-Bgl-24: 5'-AGGCAACTGTGCTATCCGAGGGAA-3'), i.e., annealed N-Bgl-12 and N-Bgl-24 oligonucleotides, SEQ ID NO: 4 and SEQ ID NO: 13 and the process of subtractive hybridization and selective amplification repeated to generate the second difference products (except that annealing and extension in PCR reactions were performed at 72° C.). Tester to driver ratios were of 1/800 to generate DP2.Testis (-HLLK), but of 1/100 to generate DP2.LB373(-skin). A third difference product DP3.Testis(-HLLK) was generated by repeating the process with J-Bgl ligated DP2.Testis(-HLLK) as tester and HLLK representation as driver, with final amplification performed of 22 cycles.

EXAMPLE 2

Search for Sequences Common to DP2.LB373[-skin] and DP3.Testis[-HLLK].

Many known tumor antigens are encoded by genes that are expressed only in tumors and in testis. By searching for sequences that were common to both DP3.Testis[-HLLK] (representing nucleic acid sequences unique to testis cells) and DP2.LB373[-skin] (representing nucleic acid sequences unique to melanoma cells), as described supra nucleic acid sequences were identified that were expressed only in testis and tumor cells that encode previously unidentified tumor antigens.

To clone DP3.Testis[-HLLK] DNA, DP3.Testis[-HLLK] was digested with DpnII and the digested DNA was ligated to BamHI digests of the commercially available plasmid pTZ18R. The bacteria, DH5αF'IQ (commercially available), was electroporated with ligated DNA. The electroporated bacteria were selected and screened by colony hybridization with a probe produced by labeling DP2.LB373 [-skin] with random primers, Klenow DNA polymerase and $\alpha$-$^{32}$P-dCTP.

Plasmids from transformants which hybridized to the DP2.LB373[-skin] probe were isolated and their inserts analyzed. One clone containing a 283 bp insert was purified and sequenced using techniques well known in the art. The sequence of the 283 bp insert shared partial homology with the MAGE gene family. Maximum homology (74%) was obtained with a 147 nucleotide sequence, corresponding to nucleotides 9895 to 10041 of MAGE-4a cDNA, as predicted from the MAGE 4a genomic DNA (Genbank accession no. U 10687), incorporated herein by reference. These data suggested that the 283 bp insert was a portion of a previously unidentified MAGE family member. This family member was designated MAGE-C1.

EXAMPLE 3

Complete MAGE-C1 cDNA

To obtain the complete MAGE-C1 cDNA, a cDNA library, prepared from LB373-MEL RNA and subcloned into pcDNAI/Amp, was screened. The cDNA library was prepared as follows.

Total RNA was extracted from LB373-MEL cells by the guanidine-isothiocyanate procedure (Davis L. G., M. D., Dibner and J. F. Battery, *Basic Methods in Molecular Biology*, Elsevier, New York, pp. 130–135 (1986)). Poly-A+ RNA was purified on oligo-dT columns (Pharmacia) and converted to cDNA using an oligo-dT (Not1, EcoRI) primer SEQ ID NO: 5. The cDNA was ligated to BstX1 adaptors (SEQ ID NO: 6), digested with Not1 and ligated with BstX1 and Not1 digested commercially available expression vector pcDNAI/Amp using methods well known in the art. Top 10F' *Escherichia coli* bacteria were electroporated with the ligated recombinant plasmids and transformants selected with ampicillin (50 μg/ml). The library was screened with a $^{32}$P-radiolabelled probe derived from the 283 bp insert isolated supra.

Bacterial transformants were screened for MAGE-C1 sequences by using methods well-known in the art. Briefly, approximately 140,000 bacteria were plated on nylon membrane filters. Duplicate nylon membrane filters were made and treated to denature and fix the bacterial DNA. A 168 bp MAGE-C1 specific probe was generated by RT-PCR (reverse transcription-PCR) using LB373-MEL RNA as template, and MAGE-C1 specific primers, i.e., sense primer SL26: 5' CCAGTAGATGAATATACAAGTT-3' which corresponds to nucleotides (nt) 2666 to nt 2687 of SEQ ID NO: 1 and antisense primer SL27: 5'-GATAGGCTGCT-TCACTT-3', which is the complementary sequence of nt 2817 to nt 2833 of SEQ ID NO: 1. This 168 bp MAGE-C1 PCR product, which corresponds to nt 2666 to 2833 of SEQ ID NO: 1, was purified on a sepharose CL-6B column, then labeled using random primers, Klenow DNA polymerase and $\alpha$-$^{32}$P-dCTP as described supra (Example 3). The treated duplicate membrane filters were hybridized with the MAGE-C1 specific probe (500,000 cpm/ml; overnight incubation at 65° C. in 5×SSC, 0.1% SDS 5× Denhardt's reagent), then washed in stringent conditions, and autoradiographed for 70 hours at room temperature. Stringent conditions as described herein refers to 0.1× to 0.5×SSC, 0.1% SDS at 65° C. for 20 min. Two colonies were identified which hybridized to the MAGE-C1 probe. The colonies were purified and screened once again to verify that they hybridized to the probe. Plasmids were isolated from these colonies and their inserts sequenced and analyzed using methods which were well-known in the art. One clone was selected and the MAGE-C1 cDNA inserted analyzed in detail. The analyzed clone contained a MAGE-C1 cDNA molecule 4031 bp long (FIG. 1) SEQ ID NO: 1. An open reading frame (ORF) runs almost through the entire cDNA with a first ATG, located at nt 257, in accordance with the known Kozak rule, and a stop codon at nt 3473. The ORF encodes a putative protein of 1072 amino acids.

Alignment with the MAGE-A1 cDNA revealed significant homologies between the MAGE-C1 cDNA (SEQ ID NO: 1) and MAGE-A1 exons 2 and 3. The open reading frame of MAGE-C1, however, is about 2 kb longer than that of MAGE A1, most of the difference being accounted for by a large repetitive sequence.

EXAMPLE 4

MAGE-C1 Expression

Sense primer SL33 (5'-CGGAGGGAGGAGACTTA-3') nt 18–34 of SEQ ID NO: 1 and antisense primer SL34 (5'-TTAAGGTGGTGCTCTAGG-3') which is complementary to nt 200–217 of SEQ ID NO: 1 are shown in FIG. 1. These primers are located in different exons, as determined by the different sizes of PCR products from cDNAs (202 bp) or genomic DNAs (approximately 1.1 kb) prepared from normal tissue and tumor cells. The expression pattern of the MAGE-C1 messenger RNA was determined by standard RT-PCR analysis of normal tissue and tumor samples. The data indicate that MAGE-C1 expression is not detected in the normal tissues tested (Table 1), with the exception of testis. Among tumor cell samples, MAGE-C1 expression is frequently detected in melanoma (46%), seminoma (100%), bladder transitional-cell carcinoma (18%), breast carcinoma (16%) and non-small cell lung carcinoma (16%). It is also detected in a significant fraction of sarcoma, head and neck carcinoma, and prostate adenocarcinoma (Table 2).

EXAMPLE 5

Northern Blot Analysis

10 μg total RNA extracted by the guanidine-isothiocyanate procedure (Davis et al., *Basic Methods in Molecular Biology*, Elsevier, New York, pp.130–135 (1986) were separated by formaldehyde agarose gel electrophoresis, transferred to a nylon membrane by capillary transfer and fixed by UV irradiation. Hybridization to the MAGE-C1 1.3 kb XbaI-EcoRI probe corresponding to nucleotide 589 to 1904 of SEQ. ID. NO: 1 (radiolabeled with [$\alpha$-$^{32}$P]dCTP) was performed overnight at 60° C. in 10% dextran sulfate, 1M NaCl, 1% SDS and 100 µg/ml denatured salmon sperm DNA. The membrane was washed consecutively in 2×SSC, 0.1% SDS for 20 min at room temperature, in 2×SSC, 0.1% SDS for 20 min at 60° C., and finally in 0.2×SSC, 0.1% SDS for 5 min at 60° C. Autoradiography was performed for 7 days using BioMax MS film (Kodak). The same membrane was-hybridized to a β-actin specific probe in identical conditions, except washing was performed twice for 10 min in 2×SSC at room temperature and autoradiography performed overnight. A MAGE-C1 messenger species migrating around 4 kb in total RNA from normal testis and some tumor cell lines was observed. No MAGE-C1 messenger species were detected in total RNA from normal lung.

EXAMPLE 6

Structure of the MAGE-C1 cDNA

Sequencing and alignment of SEQ ID NO: 1 (FIG. 2 and FIG. 3) revealed that the MAGE-C1 cDNA is homologous to MAGE-A1 (Van der Bruggen et al., *Science* 254: 1643 (1991)) only in its 3' third. Except for another short stretch of homology to the second exon of MAGE-A1, MAGE-C1 is composed of sequences unrelated to MAGE family or to any sequence reported in databanks. Compared to other MAGE cDNAs, MAGE-C1 contains an approximately 2.4 kb insertion represented in FIG. 3 by a large hatched box, which comprises 3 types of tandemly repeated sequences: 42 bp-repeats, 63 bp-repeats, and 48 bp-repeats.

EXAMPLE 7

Southern Blot Analysis

Southern blots prepared with several genomic DNAs from melanoma cell lines LB373-MEL, SK29-MEL, and LB33.A-1, (Coulie et al., *J. Exp. Med.* 180:35–42 (1994); Coulie et al., *Proc. Natl. Acad. Sci. USA* 92:7976–7980 (1995); Lehmann et al. *Eur. J. Immunol.* 25:340–347 (1995)), were hybridized with a 1.3 kb XbaI-EcoRI cDNA probe derived from SEQ ID NO: 1, which contains most of the insertion that distinguishes cDNA clone MAGE-C1 from other MAGE cDNAs. Ten µg genomic DNA digested with a restriction enzyme were separated by agarose gel electrophoresis, transferred to nylon membranes by the capillary transfer method and fixed by UV irradiation as described (Sambrook et al., *Molecular Cloning. A Laboratory Manual*, N.Y. Cold Spring Harbor Laboratory Press, pp. 9.31–9.58, incorporated here by reference). Hybridization to the [$\alpha$-$^{32}$P]dCTP radiolabeled MAGE-C1 1.3 kb XbaI-EcoRI probe was performed in 5×SSC, 5× Denhardt's, 0.1% SDS and 100 µg/ml denatured salmon sperm DNA for 12 to 24 hours at 68° C. Membranes were washed consecutively in 2×SSC, 0.1% SDS for 20 min at room temperature, in 2×SSC, 0.1% SDS for 20 min at 68° C., and in 0.2×SSC, 0.1% SDS for 20 min at 68° C. Autoradiography was performed for 3 days using BioMax MS film (Kodak).

A single hybridizing band was present in DNA from the SK29 melanoma line digested with 5 distinct restriction enzymes, suggesting that MAGE-C1 is the only gene of its type in the MAGE-family. However, PstI digested DNAs isolated from peripheral blood lymphocytes of 11 male patients contain each a unique MAGE-C1 band, but of different sizes, suggesting the existence of allelic polymorphism in gene MAGE-C1. EcoRI digested DNAs from LB373-MEL and LB33-MEL.A-1 contain a unique MAGE-C1 band of identical size (see FIG. 3 for positions of probe and restriction sites).

EXAMPLE 8

Isolation of MAGE-C1 Gene

To isolate the MAGE-C1 gene, a cosmid library prepared with genomic DNA from melanoma line LB33-MEL.A-1 was screened. Genomic DNA from melanoma line LB33-MEL.A-1 was partially digested with Mbo1 and ligated to cosmid arms of vector c2RB as described (Lurquin, C. et al., *Cell* 58:293–303 (1989)) incorporated by reference). The ligated DNA was packaged into λ phage heads (GIGA-PACK, Strategene) and titrated on *Escherichia coli* ED8767. The library was represented by 40 groups of 70,000 independent cosmids. Each group was used to infect Ed8767 bacteria, and amplified in LB medium containing 50 µg/ml ampicillin. Aliquots of 16 hour-cultures were frozen, others were titrated to evaluate the amplification of the library ($10^5$×), and the remainder of the cultures was further amplified and used to isolate total cosmid DNA, as described (De Plaen, *Immunology Methods Manual* Academic Press Ltd., 9.9: 691–718 (1997) incorporated by reference).

DNA extracted from 16 groups of approximately 70,000 independent cosmids was submitted to PCR amplification with MAGE-C1 primers. Twelve groups were found positive, and one of these was screened by colony hybridization with the XbaI-EcoRI probe. A positive cosmid, C7.2, was identified. Restriction analysis and Southern blot revealed that this cosmid contained an approximately 42 kb insert carrying 4 EcoRI fragments of 1, 1.4, 1.6, and 2 kb, respectively, and one BamHI fragment of 2 kb, which hybridized with a probe corresponding to the entire MAGE-C1 cDNA clone (SEQ ID NO: 1). Those 5 fragments were subcloned in phagemid pTZ19R and their nucleotide sequence was determined. Comparison of these sequences with the cDNA clone showed that MAGE-C1 is composed of four exons (FIG. 3). A 3,426 base pair open reading frame starts with an ATG located at the end of exon III, and runs through most part of exon IV. All repeated motifs are included in the latter but the length of this repetitive region was longer in the gDNA clone as compared to that found in the cDNA clone. Although the cDNA and genomic clones came from libraries of different origins (sublines of LB373-MEL and LB33-MEL.A-1 respectively), allelic variation could hardly explain this discrepancy, as demonstrated by Southern blot analysis with the XbaI-EcoRI probe. To confirm Southern analysis results, genomic DNA from both cell lines was amplified by PCR with primers SL38 (5'-GGCGACGACACCCAGT-3') corresponding to nt 521 to 536 of SEQ ID NO: 1 and SL43 (5'-AGGAAAGTA-GAGAGGAGACAT-3') corresponding to nt 1862 to 1882 of SEQ ID NO: 1 and products of identical sizes were obtained. Partial sequencing of these PCR products showed no difference at the nucleotide level between the two cell lines, excluding the presence of a splice site in LB373-MEL cells, that is absent in LB33-MEL cells.

To determine if reverse transcription artifacts accounted for the differing lengths of the repetitive regions in the gDNA and cDNA clones, cDNA obtained from reverse transcription of total RNA was amplified by PCR using primers SL38 and SL43.

The Transcription in vitro Systems (Promega) was used to produce MAGE-C1 RNA for the PCR amplification and cloning of MAGE-C1 repetitive region from cDNA. One µg HindIII digested pcDNAI/Amp containing MAGE-C1 cDNA clone was diluted to a final volume of 20 µl with 4 µl 5×SP6 buffer, 1 µl each NTP at 10 mM, 2 µl dithiotreitol at 0.1 M, 0.5 µl (20 Units) RNase inhibitor and 1 µl (15 units) SP6 RNA polymerase. A control reaction was set up where 5 µl [α-$^{32}$P]CTP (3000 Ci/mmol) were added to a mixture identical to the transcription mixture described above, except that only 2.4 µl of 0.1 mM CTP were used. The reactions were incubated at 37° C. for 1 hour. One µl (1U) RQ1 DNase was added to the mixtures which were incubated again for 1 hour at 37° C. One tenth of the radiolabeled RNA was analyzed by electrophoresis on a formaldehyde agarose gel, the gel was dried and autoradiographed to confirm that only full length products were obtained. Non-radioactive RNA was phenol extracted, ethanol precipitated, and resuspended in 10 µl water. One µl RNA solution was reverse transcribed in the same conditions as total RNA (Weynants et al., *Int. J. Cancer* 56:826–829 (1994)), incorporated herein by reference). To exclude contamination with plasmid DNA, a control reaction was included where no MoMLV reverse transcriptase was added. 1/40 of the completed reactions were engaged in 37 PCR cycles with SL38 sense primer and SL43 anti-sense primer. PCR products were fractionated by agarose gel electrophoresis. No detectable product were detected in control reactions.

Sense primer SL38 (5'-GGCGACGACACCCAGT-3') corresponding to nt 521 to 536 of SEQ ID NO: 1 and anti-sense primer SL43 (5'AGGAAAGTAGAGAGGAGA-CAT-3') corresponding to nt 1862 to 1882 of SEQ ID NO: 1 were used to amplify cDNA (1/40 of reverse transcription product from 2 µg total RNA) or 500 ng genomic DNA from melanoma lines LB373-MEL and LB-33-MEL.A-1. PCR was performed in 50 µl final volume, with 5 µl 10× DynaZyme buffer, 1 µl each of 10 mM dNTP, 25 pmoles each primer and 2 units DynaZyme (FynnZymes Oy), for 30 (genomic DNA) or 37 (cDNA) cycles of 1 min at 94° C., 1 min at 65° C. and 2 min at 72° C.

PCR products were ligated to plasmid pCR3 using the Eukaryotic TA Cloning Kit (Invitrogen), and ligation products were electroporated in Top10F' bacteria. Multiple products were obtained, with sizes ranging from 1.6 to 0.35 kb. In contrast, a single product was obtained from genomic DNA amplified by PCR with primers SL38 and SL43. Multiple PCR products were also generated with template cDNA obtained from reverse transcription of a full length RNA transcribed in vitro from cDNA clone MAGE-C1 (SEQ ID NO: 1). These results suggest reverse transcription artifacts are responsible for the discrepancy between genomic and cDNA clones, and that the natural mRNA species transcribed from the MAGE-C1 gene in melanoma line LB373-MEL must comprise the entire repetitive region as found in cosmid C7.2 as described supra. The sequence of a full-length cDNA of this natural mRNA is presented as SEQ ID NO: 9.

The repetitive region corresponds to a total of 18 direct repeats of 14 amino-acids (aa), 17 repeats of 21-aa, and 16 repeats of 16 aa. Gene MAGE-C1 shares maximum overall homology with gene MAGE-A10. However, comparison and alignment are made in FIGS. 2 and 3 with MAGE-A1, the most well-characterized gene of the MAGE family. Exon 1 of gene MAGE-C1 has no homologous counterparts in other MAGEs, but it is noteworthy that one Sp1 and two Ets consensus binding sites immediately precede the first exon, as has been described in MAGE-1 (De Smet et al., *Immunogenetics* 42:282–290, (1995); De Smet et al., *Proc. Natl. Acad. Sci. USA* 93:7149–7153, (1996)) and some MAGE-4 promoters (De Plaen submitted).

EXAMPLE 9

Chromosomal Localization of the MAGE-C1 Gene

Fluorescence in situ hybridization (FISH) experiments with cosmid C7.2 as a probe show that gene MAGE-C1 is located on the long arm of the X chromosome, on Xq27 band.

A human genomic cosmid probe for MAGE-C1 was used for fluorescence in situ hybridization. The entire MAGE-C1 cosmid clone was nick translated using Biotin-14 dATP and Biotin-14 dCTP (Gibco BRL) for fluorescence in situ hybridization and hybridized to normal human metaphase spreads in two independent experiments.

Chromosome preparations were obtained from phytohemagglutinin-stimulated normal peripheral blood lymphocytes cultured for 72 hours. To induce R-banding, some of the cultures were synchronized with thymidine after 48 hours, incubated at 37° C. and treated with 5'bromodeoxyuridine (BrdU) the next morning, during the final late S-phase, and harvested 6 hours later (Jacky, P. B., *Raven Press*, p. 89, (1991)). Cytogenetic harvests and slide preparations were performed using standard methods. The slides were stored at −80° C. before use.

Fluorescence in situ hybridization to metaphase chromosomes was performed as described by Pinkel et al. (Pinkel et al., *Proc. Natl. Acad. Sci. USA* 83:2934–2938, (1986) incorporated herein by reference). Briefly the biotin-labeled probe (50–100 ng) was dissolved in hybridization mixture (50% formamide, 10% dextran sulfate, 2×SSC, 0.1 µg COT-1 DNA (Gibco BRL), 10 µg sheared salmon sperm DNA as carrier) and incubated for 60 min. at 37° C. to allow the COT-1 DNA to anneal to repetitive sequences in the probe. The probe mixture was then applied to the slide and co-denatured for 10 minutes at 80° C. on a slide warmer. Hybridization was allowed to proceed overnight in a humid chamber at 37° C. The slides were washed using the formamide-wash procedure as per the FITC-biotin detection kit and, when appropriate, the amplification protocol for dual color FISH (Oncor). Biotin-labeled probe detection was accomplished by incubation with the FITC-avidin conjugate and the digoxigenin-labeled chromosome X specific α-satellite repeat probe was detected using an anti-digoxigenin-rhodamine conjugate.

Chromosome identification was performed by simultaneous hybridization with a chromosome X-specific α-satellite repeat probe (Oncor) or by R-banding using 5-bromodeoxyuridine and mounting the slides in a modified antifade mounting solution of p-phenylenediamine (pH11) (Lemieux et al., *Cytogenet. Cell Genet.* 59:311–312 (1992)) containing 0.01 µg/ml propidium iodide as counterstain to produce an R-banding pattern. Slides were examined and photographed using a Zeiss Axiophot microscope and appropriate UV-filter combinations. The 35 mm slides were scanned using a Nikon Coolscan, processed using Adobe Photoshop 4.0 and printed using a Fujix Pictrography 3000.

The chromosomal localization of the human MAGE-C1 locus was initially obtained by somatic cell hybrid mapping in experiments not described here and was independently confirmed and refined by fluorescence in situ hybridization as described, supra. In these experiments, 47 R-banded metaphase spreads from normal lymphocytes were examined for specific signals of hybridization. Signals were considered to be specific only if they were detected on each chromatid of a single chromosome. Specific signals were seen in 15 of the 47 metaphases examined (32%). In each case the hybridization signals were located in the distal portion of the X chromosome. The R-banding pattern chromosomes allowed a more specific localization of the MAGE-C1 locus to Xq26-q27.

Interestingly, other members of the MAGE family have also been localized to both the long and short arms of the X chromosome. Twelve MAGE family genes have been mapped to the distal region of the long arm of the X chromosome (De Plaen, et al., *Immunogenetics* 40:360–369, (1994); Oaks et al., *Cancer Research* 54:1627–1629, (1994)) and MAGE-Xp is located in the Xp21.3 region of the short arm in the region (Muscatelli et al., *Proc. Natl. Acad. Sci. USA* 92:4987–4991 (1995)).

EXAMPLE 10

Identification of Potential HLA Class I-Binding MAGE-C1 Peptides

Searching the MAGE-C1 protein sequence for HLA class I-binding peptides was performed on the Web site: http://bimas.dcrt.nih.gov/molbio (Parker, K. C., M. A. Bednarek, and J. E. Coligan, "Scheme for Ranking Potential HLA-A2 Binding Peptides Based on Independent Binding of Individual Peptide Side-Chains," *J. Immunol.* 152:163 (1994) incorporated in its entirety by reference). Table 3 lists peptides expected to bind to the indicated HLA class I molecules and found more than once in the MAGE-C1 protein.

EXAMPLE 11

A. Generation of Difference Products from Melanoma Tumor LB373-MEL.

A cDNA library enriched for sequences present only in melanoma cells, named tester, was generated by removing sequences that are shared with normal skin cells, called driver. The enrichment result is called a difference product (DP).

More precisely, total RNA was prepared from melanoma LB373-MEL cells (tester cells) and from a normal skin sample (driver cells), then purified on oligo-dT columns to obtain poly-A+ RNA. Poly-A+ RNA was reverse transcribed to produce cDNA. The resulting cDNA was digested with restriction enzyme Dpnll, which cuts DNA at GATC sites, generating short fragments of double stranded DNA with 5'-GATC overhangs. Double stranded adaptors with a 5'-GATC overhang (R-Bgl adaptor which is composed of annealed R-Bgl 12 and R-Bgl 24, SEQ ID NOS: 2 and 4 respectively) were ligated to the digested cDNA. The adaptor-ligated cDNA was subsequently amplified by PCR, using as primer one strand of the R-Bgl adaptor, R-Bgl 24. The resulting product is called a representation of the tester and the driver, respectively. Both representations were digested with Dpnll. Digested tester was ligated to new adaptor molecules (J-Bgl adaptor which is composed of annealed J-Bgl 12 and J-Bgl 24, SEQ ID NOS: 3 and 12 respectively). A first round of subtractive hybridization was then performed by mixing the digested driver cDNA with this J-Bgl adapted and digested tester cDNA in 100/1 proportions, denaturing the sample and incubating at 67° for 20 hours to rehybridize the denatures sample. After hybridization, the sample was PCR amplified using one strand of the J-Bgl adaptor as primer, J-Bgl 24. Hybrids constituted by two DNA strands originating from the driver population could not be amplified, as they are not ligated to the J-Bgl adaptor, while hybrids constituted by one DNA strand of each origin (tester and driver) could only be amplified linearly. Only double strands with two tester strands (representing sequences unique to the tester) were amplified exponentially. After 10 cycles of PCR amplification, the sample was treated with Mung Bean Nuclease (which digests specifically the single stranded DNA produced by the linear amplification), then submitted to 18 additional PCR cycles.

The resulting product was called difference product 1 (DP1). J-Bgl adapters on DP 1 were changed for N-Bgl-12/24 adapters (N-Bgl-12: 5'GATCTTCCCTCG-3'; N-Bgl-24: 5'-AGGCAACTGTGCTATCCGAGGGAA-3'), i.e., annealed N-Bgl-12 and N-Bgl-24 oligonucleotides, SEQ ID NO: 4 and SEQ ID NO: 13 and the process of subtractive hybridization and selective amplification repeated to generate the second difference products (except that annealing and extension in PCR reactions were performed at 72° C.). Tester to driver ratio was 1:800 to generate DP2.LB373(-skin).

DP2.LB373[-skin] was cloned in phagemid vector pTZ18R, to generate a cDNA library enriched in sequences expressed in melanoma but silent in normal skin.

B. Analysis of the Melanoma Enriched Library by Sequencing of Individual Clones.

49 individual clones isolated from the enriched melanoma library were sequenced. They correspond to 27 different genes. Search for homologies with sequences reported in databanks showed that 16 out of these 27 genes correspond to previously identified genes. Notably, two of them corresponded to gene MAGE-A3 and gene MAGE-A10, respectively, which are known to be expressed exclusively in tumors and in testis. Eleven sequences were unknown, and RT-PCR was used to determine whether they were expressed in a panel of different normal tissues. Only two out of these eleven new genes were not expressed in normal tissues except testis. The first one was named LAGE-1 and is described in U.S. patent application Ser. No. 08/791,495. The second one shares significant homologies with members of the MAGE gene family, and more particularly with gene MAGE-C1. It was therefore named MAGE-C2.

C. Search for a Complete MAGE-C2 cDNA.

The MAGE-C2 clone isolated from the enriched melanoma library is a Dpnll restriction fragment of the complete MAGE-C2 messenger. To isolate a complete MAGE-C2 cDNA, we screened a cDNA library with a MAGE-C2 probe.

The cDNA library was constructed with LB373-MEL RNA in pcDNA1/Amp as described supra. Approximately 84,000 bacteria were plated on nylon membranes. Duplicates were made and treated to denature and fix the bacterial DNA. A MAGE-C2 specific probe was generated by performing PCR on the partial MAGE-C2 clone with specific primers SL102 and SL103 (SL102: 5'AGGCGCGAAT-CAAGTTAG-3', SEQ ID NO: 15; SL103: 5'CTCCTCT-GCTGTGCTGAC-3', SEQ ID NO: 16). The 206 bp MAGE-C2 PCR product was purified on a sepharose CL-6B column, then labeled using random primers, Klenow DNA polymerase and α-$^{32}$P-dCTP. Treated duplicates were hybridized with the MAGE-C2 specific probe (500,000 cpm/ml; overnight incubation at 650°), then washed in stringent conditions (last wash performed at 65° C. in SSC 0.2×, SDS 0.1%), and autoradiographed for 70 hours. Eight positive spots resulted. A secondary screening was carried out, and a bacterial clone was obtained which contained a large open reading frame for MAGE-C2.

The MAGE-C2 cDNA is 1983 bp-long (SEQ ID NO: 18). The open reading frame starts with an ATG at position 330, and ends with a stop codon at position 1449, coding for a putative protein of 373 amino-acids (SEQ ID NO: 19).

D. Structure of the MAGE-C2 Gene.

PCR primers complementary to several regions of the MAGE-C2 cDNA were selected and the PCR products obtained after amplification of cDNA and of genomic DNA were analyzed by agarose gel electrophoresis. PCR amplification of genomic DNA with primer pairs A and B (FIG. 4) yielded products larger in size than those obtained by amplification of cDNA, revealing the existence of at least two introns in the MAGE-C2 gene. The sequences of these two introns were determined by sequencing of the PCR products. PCR amplification with primer pairs C and D (FIG. 4) yielded products of identical sizes when cDNA or genomic DNA were used as templates, suggesting that no additional intron existed in the MAGE-C2 gene. The sequence of gene MAGE-C2, as deduced from the sequence of the cDNA clone and from the sequences of the introns, is shown in SEQ ID NO: 20.

Figure 4:
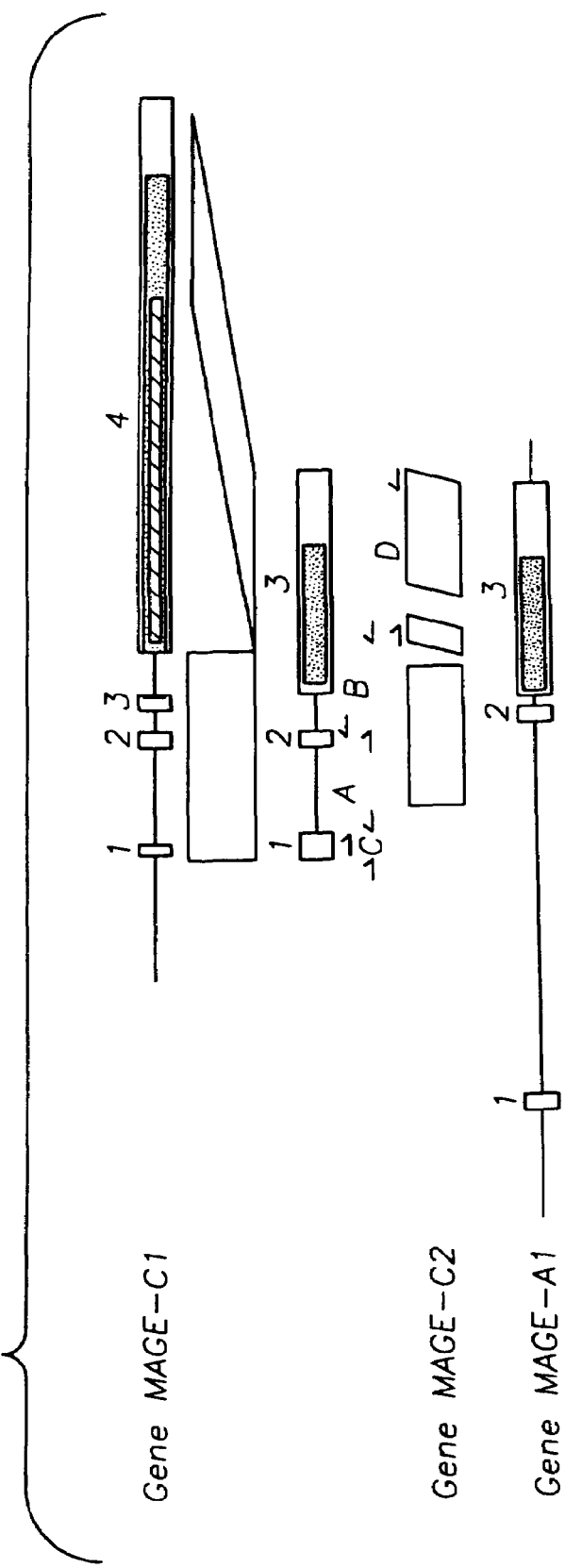
FIG. 4 is a schematic representation of genes MAGE-C1, MAGE-C2, and MAGE-A1. Exons appear as open boxes, introns as lines. Open reading frames are represented by dark boxes. Regions of homology between MAGE-C2 and the two other genes are represented by shaded areas. Important PCR primers are indicated by arrows. The hatched box represents the repetitive region found in gene MAGE-C1.

Schematic representations of genes MAGE-C2, MAGE-C1 and MAGE-A1 are shown on FIG. 4. The entire MAGE-C2 gene is homologous to gene MAGE-C1 sequences. Nonetheless, MAGE-C2 does not contain the large repetitive region that is found in the coding region of gene MAGE-C1. The exon-intron structure of gene MAGE-C2 is intermediate between that of gene MAGE-C1 and that of MAGE-A genes, represented on FIG. 4 by gene MAGE-A1. Like the MAGE-A genes, MAGE-C2 comprises three exons, but MAGE-C2 exons 1 and 2 are homologous to MAGE-C1 exons 1 and 2. The third exon of MAGE-C2 has a structure comparable to that of the third exon of the MAGE-A genes: It contains the entire open reading frame, and it starts at a similar location. The coding sequence of gene MAGE-C2 is longer than that of gene MAGE-A1, and this is due to the insertion, shortly after the start codon, of a 108 bp-sequence not found in gene MAGE-A1.

E. Expression of Gene MAGE-C2.

The expression pattern of the MAGE-C2 gene was determined by RT-PCR analysis of normal tissue and tumor samples. Selected sense primer SL102 (SEQ ID NO: 15) and antisense primer SL103 (SEQ ID NO: 16) are located in different exons (FIG. 4: primer pair A). MAGE-C2 is not expressed in a panel of normal tissues tested (Table 4), with the exception of testis. Among tumoral samples, MAGE-C2 is frequently expressed in melanoma and bladder transitional-cell carcinoma. It is also expressed in a significant fraction of head and neck carcinoma, breast carcinoma, non-small cell lung carcinoma, and sarcoma (Table 5). MAGE-C2 expression is correlated with that of other MAGE genes. 326 tumor samples were tested. Among the 63 samples that express gene MAGE-C2, 62 express also at least one MAGE-A gene. The only tumor sample that is positive for MAGE-C2 expression but negative for all other MAGE genes is a breast tumor sample. For cancer patients bearing tumors such as the latter, specific immunotherapy with MAGE antigens will rely solely on the use of MAGE-C2 derived antigens.

F. Chromosomal Location of the MAGE-C2 Gene.

The chromosomal location of the MAGE-C2 gene was determined by PCR analysis of the GeneBridge 4 Radiation Hybrid Panel (Walter et al., Nature Genet, 7:22–28 (1994) incorporated in its entirety by reference). Each DNA from the panel was submitted to PCR with primers SL102 and SL103 SEQ ID NOS: 15 and 16. PCR products were separated by agarose gel electrophoresis, blotted on a nitrocellulose membrane, and hybridized with radiolabeled primer SL118 (5'-AGCTGCCTCTGGTTGGCAGA-3' SEQ ID NO: 17). Primer SL118 is complementary to a sequence of the first intron of gene MAGE-C2. PCR results were submitted to analysis on the web site, http://www-genome.wi.mit.edu/cgi-bin/contig/rhmapper.pl. The analysis revealed that MAGE-C2 is located on the X chromosome, between markers DXS1227 and DSX7087. Gene MAGE-C1 is located between those same markers, which correspond to cytogenetic bands Xq26–Xq27.

G. MAGE-C2 and Other MAGE Proteins.

The MAGE-C2 protein shares similarities with other MAGE proteins. Multiple alignments of all known MAGE proteins show that maximal homology is observed on their COOH-terminus. Results of pairwise comparisons between the C-terminal two thirds of MAGE-C2 and the corresponding segments of other MAGE proteins are shown in Table 6. C-terminal segments of MAGE-A proteins share 52 to 94% amino-acid identity, and are closer in identity to each other than they are to MAGE-B proteins, with which they share 39 to 55% amino-acid identity. Similarly, MAGE-B proteins with 52 to 67% amino-acid identity, are closer to each other than they are to MAGE-A proteins. Based on a criteria of sequence similarity, MAGE-C1 and MAGE-C2 belong to a third subfamily: they share 68% amino-acid identity with each other, while sharing only 43 to 55% amino-acid identity with MAGE-A proteins and 39 to 46% with MAGE-B proteins.

H. Identification of Potential HLA Class I-Binding MAGE-C2 Peptides.

Searching the MAGE-C2 protein sequence for HLA class I-binding peptides was performed on the Web site: http://bimas.dcrt.nih.gov/molbio. Table 7 lists MAGE-C2 peptides expected to bind to the indicated HLA class I molecules. These HLA class I molecules were shown previously on some tumors to present peptides encoded by a gene of the MAGE family.

I. Southern Blot Analysis.

A Southern blot prepared with genomic DNAs from melanoma cell lines LB373-MEL, SK29-MEL and LB33.A-1 was hybridized with a 1.9 kb PCR amplified probe derived from SEQ ID NO: 18. Preparation of the blot was performed as described supra (Example 7). Hybridization to the [α-32P]dCTP radiolabeled MAGE-C2 probe was performed in 5×SSC, 5× Denhardt's, 0,1% SDS and 100 µg/ml denatured salmon sperm DNA for 18 hours at 68° C. Membranes were washed consecutively in 2×SSC, 0,1% SDS for 20 min. at room temperature, and in 2×SSC, 0,1% SDS for 20 min. at 68° C. Autoradiography was performed for 10 days.

Several hybridizing bands were found in the genomic DNAs obtained from the three melanoma lines. The genomic DNA were digested with BamHI or EcoRI restriction enzymes. In genomic DNAs digested with EcoRI, at least 5 bands hybridizing with the MAGE-C2 probe can be distinguished. Two of these were found to represent fragments of genes MAGE-C1 and MAGE-C2, respectively. These results suggest that MAGE-C1 and MAGE-C2, described herein, are members of a larger MAGE-C family.

TABLE 1

MAGE-C1 Expression Determined By RT-PCR On Normal Tissue Samples.

| Type of tissue | number of samples expressing MAGE-C1/ number of samples assayed |
|---|---|
| Bladder | 0/2 |
| Brain | 0/4 |
| Breast | 0/3 |
| Colon | 0/2 |
| Epididymus | 0/1 |
| Kidney | 0/1 |
| Liver | 0/4 |
| Lung | 0/6 |
| Lymphocytes (PBL) | 0/4 |
| Ovary | 0/1 |
| Placenta | 0/1 |
| Prostate | 0/2 |
| Testis | 3/3 |
| Uterus | 0/4 |

TABLE 2

MAGE-C1 Expression Determined by RT-PCR On Tumor Samples.

| Tumor type | number of samples expressing MAGE-C1/ number of samples assayed | Percent expressing MAGE-C1 |
|---|---|---|
| Cutaneous melanoma | 48/105 | 46% |
| Primary | 17/46 | 37% |
| Metastatic | 31/59 | 52% |
| Mucosis melanoma | 5/8 | |
| Uveal melanoma | 0/9 | |
| Testicular tumors | | |
| Seminoma | 9/9 | 100% |
| Non-seminoma | 0/3 | |
| Neuroblastoma | 1/3 | |
| Bladder transitional-cell carcinoma | 9/51 | 18% |
| Invasive | 9/37 | 24% |
| Superficial | 0/14 | |
| Breast carcinoma | 6/36 | 16% |
| Lung carcinoma | | |
| NSCLC | 15/95 | 16% |
| SCLC | 0/3 | |
| Sarcoma | 2/17 | 12% |
| Brain tumors | 1/9 | |
| Prostate adenocarcinoma | 2/18 | 11% |
| Head-and-neck squamous-cell carcinoma | 4/42 | 10% |
| Colorectal carcinoma | 0/30 | |
| Leukemia | 0/37 | |
| Myeloma | 0/1 | |
| Renal tumors | 0/8 | |
| Pancreatic tumors | 0/1 | |
| Ovarian tumors | 0/3 | |
| Uterine tumors | 0/9 | |
| Esophageal carcinoma | 0/6 | |
| Mesothelioma | 0/3 | |

TABLE 3

Repeated Peptides Found in Protein MAGE-C1 and Expected to Bind to HLA Class I Molecules, as Determined By Analysis on Web Site http://bimas.dcrt.nih.gov/molbio

| HLA Class I molecule | MAGE-C1 peptide (amino acid position in SEQ ID NO: 7) | Start position in the MAGE-C1 protein (amino acid in SEQ ID NO: 7) | # of repetitions |
|---|---|---|---|
| B 60 | FEGFPQSPL (aa 190–198) | 190, 260, 365, 400, 435, 470, 506 | 7 |
| B 62 | LQIPVSRSF (aa 198–206) | 198, 268 | 2 |
| B 2705 | LQIPMTSSF (aa 338–346) | 338, 408 | 2 |
| | ERTQSTFEGF (aa 254–263) | 254, 289, 324, 464 | 4 |
| B 4403 | GEDSLSPHY (aa 556–564) | 556, 571, 586 | 3 |
| B 5101 or B 5102 | FPSSTSSSL (aa 817–825) | 817, 834 | 2 |
| | SPPQGEDSL (aa 551–559) | 551, 567 | 2 |
| | EGFPQSPLQI (aa 191–200) | 191, 261, 366, 401, 436, 471, 507 | 7 |
| | FPQSPLQIPV (aa 193–202) | 193, 263, 438, 473 | 4 |
| | EGFAQSPLQI (aa 226–235) | 226, 296 | 2 |
| | FAQSPLQIPV (aa 228–237) | 228, 298 | 2 |
| B 5103 | FAQSPLQIPV (aa 228–237) | 228, 298 | 2 |
| B 5801 | RTQSTFEGF (aa 255–263) | 255, 290, 325, 265 | 4 |
| Cw 0401 | FPSSTSSSL (aa 817–825) | 817, 834 | 2 |
| | TFEGFPQSPL (aa 259–268) | 259, 364, 399, 469, 505 | 5 |
| | SFSSTLLSIF (aa 205–214) | 205, 275, 345 | 3 |
| | SFPSSTSSSL (aa 833–842) | 833, 816 | 2 |

TABLE 4

MAGE-C2 Expression in Normal Tissues, As Analyzed By RT-PCR With Primers SL102 and SL103.

| Type of Tissue | MAGE-C2 Expression |
|---|---|
| Bladder | – |
| Brain | – |
| Breast | – |
| Colon | – |
| Heart | – |
| Kidney | – |
| Liver | – |
| Lung | – |
| Lymphocytes (PBL) | – |

TABLE 4-continued

MAGE-C2 Expression in Normal Tissues, As Analyzed By RT-PCR With Primers SL102 and SL103.

| Type of Tissue | MAGE-C2 Expression |
|---|---|
| Ovary | − |
| Placenta | − |
| Skin | − |
| Suprarenals | − |
| Testis | + |
| Uterus | − |

TABLE 5

MAGE-C2 Expression in Tumoral Samples, As Analyzed by RT-PCR With Primers SL102 and SL103

| Tumor Type | Number of Positive Samples/Number Tested | |
|---|---|---|
| Cutaneous Melanoma | 30/70 | (43%) |
| Primary | 10/30 | (33%) |
| Metastatic | 20/40 | (50%) |
| Uveal Melanoma | 0/5 | |
| Bladder Transitional-Cell Carcinoma | 9/30 | |
| Invasive | 6/15 | |
| Superficial | 3/15 | |
| Head-and-Neck Squamous-Cell Carcinoma | 4/20 | |
| Breast Carcinoma | 3/20 | |
| Lung Carcinoma (NSCLC) | 4/35 | |
| Sarcoma | 2/15 | |
| Esophageal Carcinoma | 2/15 | |
| Prostate Adenocarcinoma | 1/10 | |
| Myeloma | 1/5 | |
| Brain Tumors | 0/9 | |
| Colorectal Carcinoma | 0/20 | |
| Leukemia | 0/25 | |
| Neuroblastoma | 0/2 | |
| Mesothelioma | 0/4 | |
| Renal Tumors | 0/24 | |
| Thyroide Tumors | 0/5 | |
| Uterine Tumors | 0/5 | |

TABLE 6

Percentage of Amino-Acid Identity Between C-Terminal Fragments of All Known MAGE Proteins

|    | A1 | A2 | A3 | A4 | A6 | A8 | A9 | A10 | A11 | A12 | B1 | B2 | B3 | B4 | C1 |
|----|----|----|----|----|----|----|----|-----|-----|-----|----|----|----|----|----|
| A1 |    |    |    |    |    |    |    |     |     |     |    |    |    |    |    |
| A2 | 68 |    |    |    |    |    |    |     |     |     |    |    |    |    |    |
| A3 | 68 | 83 |    |    |    |    |    |     |     |     |    |    |    |    |    |
| A4 | 77 | 66 | 66 |    |    |    |    |     |     |     |    |    |    |    |    |
| A6 | 69 | 82 | 94 | 66 |    |    |    |     |     |     |    |    |    |    |    |
| A8 | 73 | 64 | 83 | 77 | 63 |    |    |     |     |     |    |    |    |    |    |
| A9 | 65 | 58 | 60 | 68 | 57 | 72 |    |     |     |     |    |    |    |    |    |
| A10| 63 | 56 | 52 | 60 | 55 | 64 | 59 |     |     |     |    |    |    |    |    |
| A11| 62 | 56 | 56 | 62 | 56 | 62 | 63 | 62  |     |     |    |    |    |    |    |
| A12| 67 | 86 | 83 | 65 | 81 | 65 | 58 | 54  | 56  |     |    |    |    |    |    |
| B1 | 45 | 40 | 39 | 46 | 39 | 43 | 43 | 47  | 46  | 41  |    |    |    |    |    |
| B2 | 43 | 40 | 40 | 43 | 39 | 42 | 43 | 45  | 42  | 40  | 62 |    |    |    |    |
| B3 | 50 | 40 | 40 | 47 | 40 | 46 | 46 | 48  | 48  | 41  | 52 | 55 |    |    |    |
| B4 | 50 | 44 | 43 | 47 | 44 | 48 | 49 | 55  | 50  | 45  | 67 | 64 | 59 |    |    |
| C1 | 49 | 44 | 44 | 49 | 46 | 50 | 50 | 53  | 49  | 44  | 39 | 44 | 40 | 43 |    |
| C2 | 50 | 46 | 46 | 49 | 46 | 49 | 50 | 55  | 50  | 43  | 43 | 46 | 44 | 46 | 68 |

TABLE 7

Peptides Found in Protein MAGE-C2 and Expected to Bind to the Indicated HLA Class I Molecules, as Determined by Analysis on Web Site http://bimas.dcrt.nih.gov/molbio

| HLA Class I Molecule | MAGE-C2 Peptide | Position in the MAGE-C2 Protein (SEQ ID NO: 19) |
|---|---|---|
| A1 | LVEFLLLKY | aa 148–156 |
|  | YGEPRELLTK | aa 267–276 |
| A0201 | VIWEVLNAV | aa 248–256 |
|  | KVLEFLAKL | aa 313–321 |
|  | SLLIIILSV | aa 228–236 |
|  | FLAKLNNTV | aa 317–325 |
|  | KVWVQGHYL | aa 276–284 |
|  | KVAELVEFL | aa 144–152 |
|  | LLFGLALIEV | aa 191–200 |
|  | GLPDSESSFT | aa 129–138 |
|  | KVAELVEFLL | aa 144–153 |
|  | GVYAGREHFV | aa 257–266 |
| B4403 | AEMLMIVIKY | aa 165–174 |
|  | WEVLNAVGVY | aa 250–259 |
|  | REVPHSSPPY | aa 287–276 |
|  | DEKVAELVEF | aa 142–151 |

We claim:

1. An isolated tumor rejection antigen precursor (TRAP) comprising the amino acid sequence encoded by a nucleic acid molecule comprising the nucleotide sequence as set forth in SEQ ID NO: 18.

2. An isolated tumor rejection antigen precursor encoded by the isolated nucleic acid molecule of claim 1, wherein the nucleic acid molecule is a cDNA, molecule.

* * * * *

SEQUENCE LISTING (1) GENERAL INFORMATION:

(iii) NUMBER OF SEQUENCES: 20

(2) INFORMATION FOR SEQ ID NO: 1:

(i) SEQUENCE CHARACTERISTICS:
       (A) LENGTH: 4031 base pairs
       (B) TYPE: nucleic acid
       (C) STRANDEDNESS: double-stranded
       (D) TOPOLOGY: linear (xi) SEQUENCE DESCRIPTION: SEQ ID NO: 1:

```
GGATCGTCTC AGGTCAGCGG AGGGAGGAGA CTTATAGACC TATCCAGTCT TCAAGGTGCT      60

CCAGAAAGCA GGAGTTGAAG ACCTGGGTGT GAGGGACACA TACATCCTAA AGCACCACA      120

GCAGAGGAGG CCCAGGCAGT GCCAGGAGTC AAGGTTCCCA GAAGACAAAC CCCCTAGGAA     180

GACAGGCGAC CTGTGAGGCC CTAGAGCACC ACCTTAAGAG AAGAAGAGCT GTAAGCCGGC     240

CTTTGTCAGA GCCATCATGG GGGACAAGGA TATGCCTACT GCTGGGATGC CGAGTCTTCT     300

CCAGAGTTCC TCTGAGAGTC CTCAGAGTTG TCCTGAGGGG GAGGACTCCC AGTCTCCTCT     360

CCAGATTCCC CAGAGTTCTC CTGAGAGCGA CGACACCCTG TATCCTCTCC AGAGTCCTCA     420

GAGTCGTTCT GAGGGGGAGG ACTCCTCGGA TCCTCTCCAG AGACCTCCTG AGGGGAAGGA     480

CTCCCAGTCT CCTCTCCAGA TTCCCCAGAG TTCTCCTGAG GGCGACGACA CCCAGTCTCC     540

TCTCCAGAAT TCTCAGAGTT CTCCTGAGGG GAAGGACTCC CTGTCTCCTC TAGAGATTTC     600

TCAGAGCCCT CCTGAGGGTG AGGATGTCCA GTCCTCTCTG CAGAATCCTG CGAGTTCCTT     660

CTTCTCCTCT GCTTTATTGA GTATTTTCCA GAGTTCCCCT GAGAGAACTC AGAGTACTTT     720

TGAGGGTTTT CCCCAGTCTC CTCTCCAGAT TCCTGTGAGC TCCTCCTCCT CCTCCACTTT     780

ATTGAGTCTT TTCCAGAGTT CCCCTGAGAG AACTCAGAGT ACTTTTGAGG GTTTTCCCCA     840

GTCTCTTCTC CAGATTCCTA TGACCTCCTC CTTCTCCTCT ACTTTATTGA GTATTTTCCA     900

GAGTTCTCCT GAGAGTGCTC AAAGTACTTT TGAGGGTTTT CCCCAGTCTC CTCTCCAGAT     960

TCCTGGGAGC CCCTCCTTCT CCTCCACTTT ACTGAGTCTT TTCCAGAGTT CCCCTGAGAG    1020

AACTCACAGT ACTTTTGAGG GTTTTCCCCA GTCTCCTCTC CAGATTCCTA TGACCTCCTC    1080

CTTCTCCTCT ACTTTATTGA GTATTTTCCA GAGTTCTCCT GAGAGTGCTC AAAGTACTTT    1140

TGAGGGTTTT CCCCAGTCTC CTCTCCAGAT TCCTGGGAGC CCCTCCTTCT CCTCCACTTT    1200

ACTGAGTCTT TTCCAGAGTT CCCCTGAGAG AACTCACAGT ACTTTTGAGG GTTTTCCCCA    1260

GTCTCCTCTC CAGATTCCTA TGACCTCCTC CTTCTCCTCT ACTTTATTGA GTATTTACA    1320

GAGTTCTCCT GAGAGTGCTC AAAGTGCTTT TGAGGGTTTT CCCCAGTCTC CTCTCCAGAT    1380

TCCTGTGAGC TCCTCTTTCT CCTACACTTT ATTGAGTCTT TTCCAGAGTT CCCCTGAGAG    1440

AACTCAGAGT ACTTTTGAGG GTTTTCCCCA GTCTCCTCTC CAGATTCCTG TGAGCTCCTC    1500

CTCCTCCTCC TCCACTTTAT TGAGTCTTTT CCAGAGTTCC CCTGAGTGTA CTCAAAGTAC    1560

TTTTGAGGGT TTTCCCCAGT CTCCTCTCCA GATTCCTCAG AGTCCTCCTG AAGGGGAGAA    1620

TACCCATTCT CCTCTCCAGA TTGTTCCAAG TCTTCCTGAG TGGGAGGACT CCCTGTCTCC    1680

TCACTACTTT CCTCAGAGCC CTCCTCAGGG GGAGGACTCC CTATCTCCTC ACTACTTTCC    1740

TCAGAGCCCT CCTCAGGGGG AGGACTCCCT GTCTCCTCAC TACTTTCCTC AGAGCCCTCA    1800

GGGGGAGGAC TCCCTGTCTC CTCACTACTT TCCTCAGAGC CCTCCTCAGG GGGAGGACTC    1860
```

-continued

```
CATGTCTCCT CTCTACTTTC CTCAGAGTCC TCTTCAGGGG GAGGAATTCC AGTCTTCTCT    1920

CCAGAGCCCT GTGAGCATCT GCTCCTCCTC CACTCCATCC AGTCTTCCCC AGAGTTTCCC    1980

TGAGAGTTCT CAGAGTCCTC CTGAGGGGCC TGTCCAGTCT CCTCTCCATA GTCCTCAGAG    2040

CCCTCCTGAG GGGATGCACT CCCAATCTCC TCTCCAGAGT CCTGAGAGTG CTCCTGAGGG    2100

GGAGGATTCC CTGTCTCCTC TCCAAATTCC TCAGAGTCCT CTTGAGGGAG AGGACTCCCT    2160

GTCTTCTCTC CATTTTCCTC AGAGTCCTCC TGAGTGGGAG GACTCCCTCT CTCCTCTCCA    2220

CTTTCCTCAG TTTCCTCCTC AGGGGGAGGA CTTCCAGTCT TCTCTCCAGA GTCCTGTGAG    2280

TATCTGCTCC TCCTCCACTT CTTTGAGTCT TCCCCAGAGT TTCCCTGAGA GTCCTCAGAG    2340

TCCTCCTGAG GGGCCTGCTC AGTCTCCTCT CCAGAGACCT GTCAGCTCCT TCTTCTCCTA    2400

CACTTTAGCG AGTCTTCTCC AAAGTTCCCA TGAGAGTCCT CAGAGTCCTC CTGAGGGGCC    2460

TGCCCAGTCT CCTCTCCAGA GTCCTGTGAG CTCCTTCCCC TCCTCCACTT CATCGAGTCT    2520

TTCCCAGAGT TCTCCTGTGA GCTCCTTCCC CTCCTCCACT TCATCGAGTC TTTCCAAGAG    2580

TTCCCCTGAG AGTCCTCTCC AGAGTCCTGT GATCTCCTTC TCCTCCTCCA CTTCATTGAG    2640

CCCATTCAGT GAAGAGTCCA GCAGCCCAGT AGATGAATAT ACAAGTTCCT CAGACACCTT    2700

GCTAGAGAGT GATTCCTTGA CAGACAGCGA GTCCTTGATA GAGAGCGAGC CCTTGTTCAC    2760

TTATACACTG GATGAAAAGG TGGACGAGTT GGCGCGGTTT CTTCTCCTCA AATATCAAGT    2820

GAAGCAGCCT ATCACAAAGG CAGAGATGCT GACGAATGTC ATCAGCAGGT ACACGGGCTA    2880

CTTTCCTGTG ATCTTCAGGA AAGCCCGTGA GTTCATAGAG ATACTTTTTG GCATTTCCCT    2940

GAGAGAAGTG GACCCTGATG ACTCCTATGT CTTTGTAAAC ACATTAGACC TCACCTCTGA    3000

GGGGTGTCTG AGTGATGAGC AGGGCATGTC CCAGAACCGC CTCCTGATTC TTATTCTGAG    3060

TATCATCTTC ATAAAGGGCA CCTATGCCTC TGAGGAGGTC ATCTGGGATG TGCTGAGTGG    3120

AATAGGGGTG CGTGCTGGGA GGGAGCACTT TGCCTTTGGG GAGCCCAGGG AGCTCCTCAC    3180

TAAAGTTTGG GTGCAGGAAC ATTACCTAGA GTACCGGGAG GTGCCCAACT CTTCTCCTCC    3240

TCGTTACGAA TTCCTGTGGG GTCCAAGAGC TCATTCAGAA GTCATTAAGA GGAAAGTAGT    3300

AGAGTTTTTG GCCATGCTAA AGAATACCGT CCCTATTACC TTTCCATCCT CTTACAAGGA    3360

TGCTTTGAAA GATGTGGAAG AGAGAGCCCA GGCCATAATT GACACCACAG ATGATTCGAC    3420

TGCCACAGAA AGTGCAAGCT CCAGTGTCAT GTCCCCCAGC TTCTCTTCTG AGTGAAGTCT    3480

AGGGCAGATT CTTCCCTCTG AGTTTGAAGG GGGCAGTCGA GTTTCTACGT GGTGGAGGGC    3540

CTGGTTGAGG CTGGAGAGAA CACAGTGCTA TTTGCATTTC TGTTCCATAT GGGTAGTTAT    3600

GGGGTTTACC TGTTTTACTT TTGGGTATTT TTCAAATGCT TTTCCTATTA ATAACAGGTT    3660

TAAATAGCTT CAGAATCCTA GTTTATGCAC ATGAGTCGCA CATGTATTGC TGTTTTTCTG    3720

GTTTAAGAGT AACAGTTTGA TATTTTGTAA AAACAAAAAC ACACCCAAAC ACACCACATT    3780

GGGAAAACCT TCTGCCTCAT TTTGTGATGT GTCACAGGTT AATGTGGTGT TACTGTAGGA    3840

ATTTTCTTGA AACTGTGAAG GAACTCTGCA GTTAAATAGT GGAATAAAGT AAAGGATTGT    3900

TAATGTTTGC ATTTCCTCAG GTCCTTTAGT CTGTTGTTCT TGAAAACTAA AGATACATAC    3960

CTGGTTTGCT TGGCTTACGT AAGAAAGTAG AAGAAAGTAA ACTGTAATAA ATAAAAAAAA    4020

AAAAAAAAAA A                                                        4031
```

(2) INFORMATION FOR SEQ ID NO: 2:

(i) SEQUENCE CHARACTERISTICS:
        (A) LENGTH: 12 base pairs

```
           (B) TYPE: nucleic acid
           (C) STRANDEDNESS: single-stranded
           (D) TOPOLOGY: linear (xi) SEQUENCE DESCRIPTION: SEQ ID NO: 2:

GATCTGCGGT GA                                                              12

(2) INFORMATION FOR SEQ ID NO: 3:

(i) SEQUENCE CHARACTERISTICS:
           (A) LENGTH: 12 base pairs
           (B) TYPE: nucleic acid
           (C) STRANDEDNESS: SINGLE-stranded
           (D) TOPOLOGY: linear (xi) SEQUENCE DESCRIPTION: SEQ ID NO: 3:

GATCTGTTCA TG                                                              12

(2) INFORMATION FOR SEQ ID NO: 4:

(i) SEQUENCE CHARACTERISTICS:
           (A) LENGTH: 12 base pairs
           (B) TYPE: nucleic acid
           (C) STRANDEDNESS: single-stranded
           (D) TOPOLOGY: linear (xi) SEQUENCE DESCRIPTION: SEQ ID NO: 4:

GATCTTCCCT CG                                                              12

(2) INFORMATION FOR SEQ ID NO: 5:

(i) SEQUENCE CHARACTERISTICS:
           (A) LENGTH: 46 base pairs
           (B) TYPE: nucleic acid
           (C) STRANDEDNESS: single-stranded
           (D) TOPOLOGY: linear (xi) SEQUENCE DESCRIPTION: SEQ ID NO: 5:

NAACTGGAAG AATTCGCGGC CGCAGGAATT TTTTTTTTTT TTTTTT                          46

(2) INFORMATION FOR SEQ ID NO: 6:

(i) SEQUENCE CHARACTERISTICS:
           (A) LENGTH: 12 base pairs
           (B) TYPE: nucleic acid
           (C) STRANDEDNESS: single-stranded
           (D) TOPOLOGY: linear (ix) FEATURE:
           (D) OTHER INFORMATION: BstX1 adapter upper strand (xi) SEQUENCE DESCRIPTION: SEQ ID NO: 6:

CTTTCCAGCA CA                                                              12

(2) INFORMATION FOR SEQ ID NO: 7:

(i) SEQUENCE CHARACTERISTICS:
           (A) LENGTH: 1142
           (B) TYPE: amino acids
           (C) STRANDEDNESS: single-stranded
           (D) TOPOLOGY: linear (xi) SEQUENCE DESCRIPTION: SEQ ID NO: 7:

Met Gly Asp Lys Asp Met Pro Thr Ala Gly Met Pro Ser Leu Leu Gln
                 5                  10                  15
Ser Ser Ser Glu Ser Pro Gln Ser Cys Pro Glu Gly Glu Asp Ser Gln
         20                  25                  30
```

-continued

```
Ser Pro Leu Gln Ile Pro Gln Ser Pro Glu Ser Asp Asp Thr Leu
         35                  40                  45
Tyr Pro Leu Gln Ser Pro Gln Ser Arg Ser Glu Gly Glu Asp Ser Ser
 50                  55                  60
Asp Pro Leu Gln Arg Pro Pro Glu Gly Lys Asp Ser Gln Ser Pro Leu
 65                  70                  75                  80
Gln Ile Pro Gln Ser Ser Pro Glu Gly Asp Asp Thr Gln Ser Pro Leu
                 85                  90                  95
Gln Asn Ser Gln Ser Ser Pro Glu Gly Lys Asp Ser Leu Ser Pro Leu
                100                 105                 110
Glu Ile Ser Gln Ser Pro Pro Glu Gly Glu Asp Val Gln Ser Pro Leu
            115                 120                 125
Gln Asn Pro Ala Ser Ser Phe Phe Ser Ser Ala Leu Leu Ser Ile Phe
        130                 135                 140
Gln Ser Ser Pro Glu Ser Ile Gln Ser Pro Phe Glu Gly Phe Pro Gln
145                 150                 155                 160
Ser Val Leu Gln Ile Pro Val Ser Ala Ala Ser Ser Ser Thr Leu Val
                165                 170                 175
Ser Ile Phe Gln Ser Ser Pro Glu Ser Thr Gln Ser Pro Phe Glu Gly
            180                 185                 190
Phe Pro Gln Ser Pro Leu Gln Ile Pro Val Ser Arg Ser Phe Ser Ser
        195                 200                 205
Thr Leu Leu Ser Ile Phe Gln Ser Ser Pro Glu Arg Ser Gln Arg Thr
210                 215                 220
Ser Glu Gly Phe Ala Gln Ser Pro Leu Gln Ile Pro Val Ser Ser Ser
225                 230                 235                 240
Ser Ser Ser Thr Leu Leu Ser Leu Phe Gln Ser Ser Pro Glu Arg Thr
                245                 250                 255
Gln Ser Thr Phe Glu Gly Phe Pro Gln Ser Pro Leu Gln Ile Pro Val
            260                 265                 270
Ser Arg Ser Phe Ser Ser Thr Leu Leu Ser Ile Phe Gln Ser Ser Pro
        275                 280                 285
Glu Arg Thr Gln Ser Thr Phe Glu Gly Phe Ala Gln Ser Pro Leu Gln
290                 295                 300
Ile Pro Val Ser Ser Ser Ser Ser Thr Leu Leu Ser Leu Phe Gln
305                 310                 315                 320
Ser Ser Pro Glu Arg Thr Gln Ser Thr Phe Glu Gly Phe Pro Gln Ser
                325                 330                 335
Leu Leu Gln Ile Pro Met Thr Ser Ser Phe Ser Ser Thr Leu Leu Ser
            340                 345                 350
Ile Phe Gln Ser Ser Pro Glu Ser Ala Gln Ser Thr Phe Glu Gly Phe
        355                 360                 365
Pro Gln Ser Pro Leu Gln Ile Pro Gly Ser Pro Ser Phe Ser Ser Thr
    370                 375                 380
Leu Leu Ser Leu Phe Gln Ser Ser Pro Glu Arg Thr His Ser Thr Phe
385                 390                 395                 400
Glu Gly Phe Pro Gln Ser Pro Leu Gln Ile Pro Met Thr Ser Ser Phe
                405                 410                 415
Ser Ser Thr Leu Leu Ser Ile Leu Gln Ser Ser Pro Glu Ser Ala Gln
            420                 425                 430
Ser Ala Phe Glu Gly Phe Pro Gln Ser Pro Leu Gln Ile Pro Val Ser
        435                 440                 445
```

-continued

```
Ser Ser Phe Ser Tyr Thr Leu Leu Ser Leu Phe Gln Ser Ser Pro Glu
    450                 455                 460

Arg Thr Gln Ser Thr Phe Glu Gly Phe Pro Gln Ser Pro Leu Gln Ile
465                 470                 475                 480

Pro Val Ser Ser Ser Ser Ser Ser Thr Leu Leu Ser Leu Phe Gln
                485                 490                 495

Ser Ser Pro Glu Cys Thr Gln Ser Thr Phe Glu Gly Phe Pro Gln Ser
            500                 505                 510

Pro Leu Gln Ile Pro Gln Ser Pro Glu Gly Glu Asn Thr His Ser
        515                 520                 525

Pro Leu Gln Ile Val Pro Ser Leu Pro Glu Trp Glu Asp Ser Leu Ser
    530                 535                 540

Pro His Tyr Phe Pro Gln Ser Pro Gln Gly Glu Asp Ser Leu Ser
545                 550                 555                 560

Pro His Tyr Phe Pro Gln Ser Pro Gln Gly Glu Asp Ser Leu Ser
                565                 570                 575

Pro His Tyr Phe Pro Gln Ser Pro Gln Gly Glu Asp Ser Leu Ser Pro
            580                 585                 590

His Tyr Phe Pro Gln Ser Pro Gln Gly Glu Asp Ser Met Ser Pro
        595                 600                 605

Leu Tyr Phe Pro Gln Ser Pro Leu Gln Gly Glu Glu Phe Gln Ser Ser
    610                 615                 620

Leu Gln Ser Pro Val Ser Ile Cys Ser Ser Thr Pro Ser Ser Leu
625                 630                 635                 640

Pro Gln Ser Phe Pro Glu Ser Ser Gln Ser Pro Pro Glu Gly Pro Val
                645                 650                 655

Gln Ser Pro Leu His Ser Pro Gln Ser Pro Pro Glu Gly Met His Ser
            660                 665                 670

Gln Ser Pro Leu Gln Ser Pro Glu Ser Ala Pro Glu Gly Glu Asp Ser
        675                 680                 685

Leu Ser Pro Leu Gln Ile Pro Gln Ser Pro Leu Glu Gly Glu Asp Ser
    690                 695                 700

Leu Ser Ser Leu His Phe Pro Gln Ser Pro Pro Glu Trp Glu Asp Ser
705                 710                 715                 720

Leu Ser Pro Leu His Phe Pro Gln Phe Pro Gln Gly Glu Asp Phe
                725                 730                 735

Gln Ser Ser Leu Gln Ser Pro Val Ser Ile Cys Ser Ser Thr Ser
            740                 745                 750

Leu Ser Leu Pro Gln Ser Phe Pro Glu Ser Pro Gln Ser Pro Pro Glu
        755                 760                 765

Gly Pro Ala Gln Ser Pro Leu Gln Arg Pro Val Ser Ser Phe Phe Ser
    770                 775                 780

Tyr Thr Leu Ala Ser Leu Leu Gln Ser Ser His Glu Ser Pro Gln Ser
785                 790                 795                 800

Pro Pro Glu Gly Pro Ala Gln Ser Pro Leu Gln Ser Pro Val Ser Ser
                805                 810                 815

Phe Pro Ser Ser Thr Ser Ser Ser Leu Ser Gln Ser Ser Pro Val Ser
            820                 825                 830

Ser Phe Pro Ser Ser Thr Ser Ser Ser Leu Ser Lys Ser Ser Pro Glu
        835                 840                 845

Ser Pro Leu Gln Ser Pro Val Ile Ser Phe Ser Ser Thr Ser Leu
    850                 855                 860

Ser Pro Phe Ser Glu Glu Ser Ser Ser Pro Val Asp Glu Tyr Thr Ser
```

-continued

```
                          865                 870                 875                 880
                      Ser Ser Asp Thr Leu Leu Glu Ser Asp Ser Leu Thr Asp Ser Glu Ser
                                      885                 890                 895

Leu Ile Glu Ser Glu Pro Leu Phe Thr Tyr Thr Leu Asp Glu Lys Val
                                  900                 905                 910

Asp Glu Leu Ala Arg Phe Leu Leu Lys Tyr Gln Val Lys Gln Pro
                              915                 920                 925

Ile Thr Lys Ala Glu Met Leu Thr Asn Val Ile Ser Arg Tyr Thr Gly
                              930                 935                 940

Tyr Phe Pro Val Ile Phe Arg Lys Ala Arg Glu Phe Ile Glu Ile Leu
                      945                 950                 955                 960

Phe Gly Ile Ser Leu Arg Glu Val Asp Pro Asp Asp Ser Tyr Val Phe
                                      965                 970                 975

Val Asn Thr Leu Asp Leu Thr Ser Glu Gly Cys Leu Ser Asp Glu Gln
                                  980                 985                 990

Gly Met Ser Gln Asn Arg Leu Leu Ile Leu Ile Leu Ser Ile Ile Phe
                                  995                1000                1005

Ile Lys Gly Thr Tyr Ala Ser Glu Glu Val Ile Trp Asp Val Leu Ser
                          1010                1015                1020

Gly Ile Gly Val Arg Ala Gly Arg Glu His Phe Ala Phe Gly Glu Pro
                      1025                1030                1035                1040

Arg Glu Leu Leu Thr Lys Val Trp Val Gln Glu His Tyr Leu Glu Tyr
                                      1045                1050                1055

Arg Glu Val Pro Asn Ser Ser Pro Arg Tyr Glu Phe Leu Trp Gly
                                  1060                1065                1070

Pro Arg Ala His Ser Glu Val Ile Lys Arg Lys Val Val Glu Phe Leu
                              1075                1080                1085

Ala Met Leu Lys Asn Thr Val Pro Ile Thr Phe Pro Ser Ser Tyr Lys
                              1090                1095                1100

Asp Ala Leu Lys Asp Val Glu Glu Arg Ala Gln Ala Ile Ile Asp Thr
                      1105                1110                1115                1120

Thr Asp Asp Ser Thr Ala Thr Glu Ser Ala Ser Ser Ser Val Met Ser
                                      1125                1130                1135

Pro Ser Phe Ser Ser Glu
                                      1140

(2) INFORMATION FOR SEQ ID NO: 8:

(i) SEQUENCE CHARACTERISTICS:
        (A) LENGTH: 1691 base pairs
        (B) TYPE: nucleotides
        (C) STRANDEDNESS: single stranded
        (D) TOPOLOGY: linear (xi) SEQUENCE DESCRIPTION: SEQ ID NO: 8:

CCATTCTGAG GGACGGCGTA GAGTTCGGCC GAAGGAACCT GACCCAGGCT CTGTGAGGAG     60

GCAAGGTTTT CAGGGACAG GCCAACCCAG AGGACAGGAT TCCCTGGAGG CCACAGAGGA    120

GCACCAAGGA GAAGATCTGC CTGTGGGTCT TCATTGCCCA GCTCCTGCCC ACACTCCTGC    180

CTGCTGCCCT GACGAGAGTC ATCATGTCTC TTGAGCAGAG GAGTCTGCAC TGCAAGCCTG    240

AGGAAGCCCT TGAGGCCCAA CAAGAGGCCC TGGGCCTGGT GTGTGTGCAG GCTGCCACCT    300

CCTCCTCCTC TCCTCTGGTC CTGGGCACCC TGGAGGAGGT GCCCACTGCT GGGTCAACAG    360

ATCCTCCCCA GAGTCCTCAG GGAGCCTCCG CCTTTCCCAC TACCATCAAC TTCACTCGAC    420

AGAGGCAACC CAGTGAGGGT TCCAGCAGCC GTGAAGAGGA GGGGCCAAGC ACCTCTTGTA    480
```

```
TCCTGGAGTC CTTGTTCCGA GCAGTAATCA CTAAGAAGGT GGCTGATTTG GTTGGTTTTC      540

TGCTCCTCAA ATATCGAGCC AGGGAGCCAG TCACAAAGGC AGAAATGCTG GAGAGTGTCA      600

TCAAAAATTA CAAGCACTGT TTTCCTGAGA TCTTCGGCAA AGCCTCTGAG TCCTTGCAGC      660

TGGTCTTTGG CATTGACGTG AAGGAAGCAG ACCCCACCGG CCACTCCTAT GTCCTTGTCA      720

CCTGCCTAGG TCTCTCCTAT GATGGCCTGC TGGGTGATAA TCAGATCATG CCCAAGACAG      780

GCTTCCTGAT AATTGTCCTG GTCATGATTG CAATGGAGGG CGGCCATGCT CCTGAGGAGG      840

AAATCTGGGA GGAGCTGAGT GTGATGGAGG TGTATGATGG GAGGGAGCAC AGTGCCTATG      900

GGGAGCCCAG GAAGCTGCTC ACCCAAGATT TGGTGCAGGA AAAGTACCTG GAGTACCGGC      960

AGGTGCCGGA CAGTGATCCC GCACGCTATG AGTTCCTGTG GGGTCCAAGG GCCCTCGCTG     1020

AAACCAGCTA TGTGAAAGTC CTTGAGTATG TGATCAAGGT CAGTGCAAGA GTTCGCTTTT     1080

TCTTCCCATC CCTGCGTGAA GCAGCTTTGA GAGAGGAGGA AGAGGGAGTC TGAGCATGAG     1140

TTGCAGCCAA GGCCAGTGGG AGGGGACTG GGCCAGTGCA CCTTCCAGGG CCGCGTCCAG      1200

CAGCTTCCCC TGCCTCGTGT GACATGAGGC CCATTCTTCA CTCTGAAGAG AGCGGTCAGT     1260

GTTCTCAGTA GTAGGTTTCT GTTCTATTGG GTGACTTGGA GATTTATCTT TGTTCTCTTT     1320

TGGAATTGTT CAAATGTTTT TTTTTAAGGG ATGGTTGAAT GAACTTCAGC ATCCAAGTTT     1380

ATGAATGACA GCAGTCACAC AGTTCTGTGT ATATAGTTTA AGGGTAAGAG TCTTGTGTTT     1440

TATTCAGATT GGGAAATCCA TTCTATTTTG TGAATTGGGA TAATAACAGC AGTGGAATAA     1500

GTACTTAGAA ATGTGAAAAA TGAGCAGTAA AATAGATGAG ATAAAGAACT AAAGAAATTA     1560

AGAGATAGTC AATTCTTGCC TTATACCTCA GTCTATTCTG TAAAATTTTT AAAGATATAT     1620

GCATACCTGG ATTTCCTTGG CTTCTTTGAG AATGTAAGAG AAATTAAATC TGAATAAAGA     1680

ATTCTTCCTG T                                                        1691
```

(2) INFORMATION FOR SEQ ID NO: 9:

(i) SEQUENCE CHARACTERISTICS:
    (A) LENGTH: 4225 base pairs
    (B) TYPE: nucleic acids
    (C) STRANDEDNESS: double-stranded
    (D) TOPOLOGY: linear (xi) SEQUENCE DESCRIPTION: SEQ ID NO: 9:

```
GGATCGTCTC AGGTCAGCGG AGGGAGGAGA CTTATAGACC TATCCAGTCT TCAAGGTGCT       60

CCAGAAAGCA GGAGTTGAAG ACCTGGGTGT GAGGGACACA TACATCCTAA AAGCACCACA      120

GCAGAGGAGG CCCAGGCAGT GCCAGGAGTC AAGGTTCCCA GAAGACAAAC CCCCTAGGAA      180

GACAGGCGAC CTGTGAGGCC CTAGAGCACC ACCTTAAGAG AAGAAGAGCT GTAAGCCGGC      240

CTTTGTCAGA GCCATCATGG GGGACAAGGA TATGCCTACT GCTGGGATGC CGAGTCTTCT      300

CCAGAGTTCC TCTGAGAGTC CTCAGAGTTG TCCTGAGGGG GAGGACTCCC AGTCTCCTCT      360

CCAGATTCCC CAGAGTTCTC CTGAGAGCGA CGACACCCTG TATCCTCTCC AGAGTCCTCA      420

GAGTCGTTCT GAGGGGGAGG ACTCCTCGGA TCCTCTCCAG AGACCTCCTG AGGGGAAGGA      480

CTCCCAGTCT CCTCTCCAGA TTCCCCAGAG TTCTCCTGAG GGCGACGACA CCCAGTCTCC      540

TCTCCAGAAT TCTCAGAGTT CTCCTGAGGG GAAGGACTCC CTGTCTCCTC TAGAGATTTC      600

TCAGAGCCCT CCTGAGGGTG AGGATGTCCA GTCTCCTCTG CAGAATCCTG CGAGTTCCTT      660

CTTCTCCTCT GCTTTATTGA GTATTTTCCA GAGTTCCCCT GAGAGTATTC AAAGTCCTTT      720

TGAGGGTTTT CCCCAGTCTG TTCTCCAGAT TCCTGTGAGC GCCGCCTCCT CCTCCACTTT      780
```

```
AGTGAGTATT TTCCAGAGTT CCCCTGAGAG TACTCAAAGT CCTTTTGAGG GTTTTCCCCA    840

GTCTCCACTC CAGATTCCTG TGAGCCGCTC CTTCTCCTCC ACTTTATTGA GTATTTTCCA    900

GAGTTCCCCT GAGAGAAGTC AGAGAACTTC TGAGGGTTTT GCACAGTCTC CTCTCCAGAT    960

TCCTGTGAGC TCCTCCTCGT CCTCCACTTT ACTGAGTCTT TTCCAGAGTT CCCCTGAGAG   1020

AACTCAGAGT ACTTTTGAGG GTTTTCCCCA GTCTCCACTC CAGATTCCTG TGAGCCGCTC   1080

CTTCTCCTCC ACTTTATTGA GTATTTTCCA GAGTTCCCCT GAGAGAACTC AGAGTACTTT   1140

TGAGGGTTTT GCCCAGTCTC CTCTCCAGAT TCCTGTGAGC TCCTCCTCCT CCTCCACTTT   1200

ATTGAGTCTT TTCCAGAGTT CCCCTGAGAG AACTCAGAGT ACTTTTGAGG GTTTTCCCCA   1260

GTCTCTTCTC CAGATTCCTA TGACCTCCTC CTTCTCCTCT ACTTTATTGA GTATTTTCCA   1320

GAGTTCTCCT GAGAGTGCTC AAAGTACTTT TGAGGGTTTT CCCCAGTCTC CTCTCCAGAT   1380

TCCTGGGAGC CCCTCCTTCT CCTCCACTTT ACTGAGTCTT TTCCAGAGTT CCCCTGAGAG   1440

AACTCACAGT ACTTTTGAGG GTTTTCCCCA GTCTCCTCTC CAGATTCCTA TGACCTCCTC   1500

CTTCTCCTCT ACTTTATTGA GTATTTTACA GAGTTCTCCT GAGAGTGCTC AAAGTGCTTT   1560

TGAGGGTTTT CCCCAGTCTC CTCTCCAGAT TCCTGTGAGC TCCTCTTTCT CCTACACTTT   1620

ATTGAGTCTT TTCCAGAGTT CCCCTGAGAG AACTCAGAGT ACTTTTGAGG GTTTTCCCCA   1680

GTCTCCTCTC CAGATTCCTG TGAGCTCCTC CTCCTCCTCC TCCACTTTAT TGAGTCTTTT   1740

CCAGAGTTCC CCTGAGTGTA CTCAAAGTAC TTTTGAGGGT TTTCCCCAGT CTCCTCTCCA   1800

GATTCCTCAG AGTCCTCCTG AAGGGGAGAA TACCCATTCT CCTCTCCAGA TTGTTCCAAG   1860

TCTTCCTGAG TGGGAGGACT CCCTGTCTCC TCACTACTTT CCTCAGAGCC CTCCTCAGGG   1920

GGAGGACTCC CTATCTCCTC ACTACTTTCC TCAGAGCCCT CCTCAGGGGG AGGACTCCCT   1980

GTCTCCTCAC TACTTTCCTC AGAGCCCTCA GGGGAGGAC TCCCTGTCTC CTCACTACTT   2040

TCCTCAGAGC CCTCCTCAGG GGGAGGACTC CATGTCTCCT CTCTACTTTC CTCAGAGTCC   2100

TCTTCAGGGG GAGGAATTCC AGTCTTCTCT CCAGAGCCCT GTGAGCATCT GCTCCTCCTC   2160

CACTCCATCC AGTCTTCCCC AGAGTTTCCC TGAGAGTTCT CAGAGTCCTC CTGAGGGGCC   2220

TGTCCAGTCT CCTCTCCATA GTCCTCAGAG CCCTCCTGAG GGGATGCACT CCCAATCTCC   2280

TCTCCAGAGT CCTGAGAGTG CTCCTGAGGG GGAGGATTCC CTGTCTCCTC TCCAAATTCC   2340

TCAGAGTCCT CTTGAGGGAG AGGACTCCCT GTCTTCTCTC CATTTTCCTC AGAGTCCTCC   2400

TGAGTGGGAG GACTCCCTCT CTCCTCTCCA CTTTCCTCAG TTTCCTCCTC AGGGGGAGGA   2460

CTTCCAGTCT TCTCTCCAGA GTCCTGTGAG TATCTGCTCC TCCTCCACTT CTTTGAGTCT   2520

TCCCCAGAGT TTCCCTGAGA GTCCTCAGAG TCCTCCTGAG GGGCCTGCTC AGTCTCCTCT   2580

CCAGAGACCT GTCAGCTCCT TCTTCTCCTA CACTTTAGCG AGTCTTCTCC AAAGTTCCCA   2640

TGAGAGTCCT CAGAGTCCTC CTGAGGGGCC TGCCCAGTCT CCTCTCCAGA GTCCTGTGAG   2700

CTCCTTCCCC TCCTCCACTT CATCGAGTCT TTCCAGAGT TCTCCTGTGA GCTCCTTCCC   2760

CTCCTCCACT TCATCGAGTC TTTCCAAGAG TTCCCCTGAG AGTCCTCTCC AGAGTCCTGT   2820

GATCTCCTTC TCCTCCTCCA CTTCATTGAG CCCATTCAGT GAAGAGTCCA GCAGCCCAGT   2880

AGATGAATAT ACAAGTTCCT CAGACACCTT GCTAGAGAGT GATTCCTTGA CAGACAGCGA   2940

GTCCTTGATA GAGAGCGAGC CCTTGTTCAC TTATACACTG GATGAAAAGG TGGACGAGTT   3000

GGCGCGGTTT CTTCTCCTCA AATATCAAGT GAAGCAGCCT ATCACAAAGG CAGAGATGCT   3060

GACGAATGTC ATCAGCAGGT ACACGGGCTA CTTTCCTGTG ATCTTCAGGA AAGCCCGTGA   3120

GTTCATAGAG ATACTTTTTG GCATTTCCCT GAGAGAAGTG GACCCTGATG ACTCCTATGT   3180
```

-continued

| | |
|---|---|
| CTTTGTAAAC ACATTAGACC TCACCTCTGA GGGGTGTCTG AGTGATGAGC AGGGCATGTC | 3240 |
| CCAGAACCGC CTCCTGATTC TTATTCTGAG TATCATCTTC ATAAAGGGCA CCTATGCCTC | 3300 |
| TGAGGAGGTC ATCTGGGATG TGCTGAGTGG AATAGGGGTG CGTGCTGGGA GGGAGCACTT | 3360 |
| TGCCTTTGGG GAGCCCAGGG AGCTCCTCAC TAAAGTTTGG GTGCAGGAAC ATTACCTAGA | 3420 |
| GTACCGGGAG GTGCCCAACT CTTCTCCTCC TCGTTACGAA TTCCTGTGGG GTCCAAGAGC | 3480 |
| TCATTCAGAA GTCATTAAGA GGAAAGTAGT AGAGTTTTTG GCCATGCTAA AGAATACCGT | 3540 |
| CCCTATTACC TTTCCATCCT CTTACAAGGA TGCTTTGAAA GATGTGGAAG AGAGAGCCCA | 3600 |
| GGCCATAATT GACACCACAG ATGATTCGAC TGCCACAGAA AGTGCAAGCT CCAGTGTCAT | 3660 |
| GTCCCCCAGC TTCTCTTCTG AGTGAAGTCT AGGGCAGATT CTTCCCTCTG AGTTTGAAGG | 3720 |
| GGGCAGTCGA GTTTCTACGT GGTGGAGGGC CTGGTTGAGG CTGGAGAGAA CACAGTGCTA | 3780 |
| TTTGCATTTC TGTTCCATAT GGGTAGTTAT GGGGTTTACC TGTTTTACTT TTGGGTATTT | 3840 |
| TTCAAATGCT TTTCCTATTA ATAACAGGTT TAAATAGCTT CAGAATCCTA GTTTATGCAC | 3900 |
| ATGAGTCGCA CATGTATTGC TGTTTTTCTG GTTTAAGAGT AACAGTTTGA TATTTTGTAA | 3960 |
| AAACAAAAAC ACACCCAAAC ACACCACATT GGGAAAACCT TCTGCCTCAT TTTGTGATGT | 4020 |
| GTCACAGGTT AATGTGGTGT TACTGTAGGA ATTTTCTTGA AACTGTGAAG GAACTCTGCA | 4080 |
| GTTAAATAGT GGAATAAAGT AAAGGATTGT TAATGTTTGC ATTTCCTCAG GTCCTTTAGT | 4140 |
| CTGTTGTTCT TGAAAACTAA AGATACATAC CTGGTTTGCT TGGCTTACGT AAGAAAGTAG | 4200 |
| AAGAAAGTAA ACTGTAATAA ATAAA | 4225 |

(2) INFORMATION FOR SEQ ID NO: 10:

(i) SEQUENCE CHARACTERISTICS:
        (A) LENGTH: 309
        (B) TYPE: amino acids
        (C) STRANDEDNESS: single stranded
        (D) TOPOLOGY: linear (xi) SEQUENCE DESCRIPTION: SEQ ID NO: 10:

Met Ser Leu Glu Gln Arg Ser Leu His Cys Lys Pro Glu Glu Ala Leu
              5                    10                 15

Glu Ala Gln Gln Glu Ala Leu Gly Leu Val Cys Val Gln Ala Ala Thr
          20                    25                    30

Ser Ser Ser Ser Pro Leu Val Leu Gly Thr Leu Glu Glu Val Pro Thr
          35                    40                    45

Ala Gly Ser Thr Asp Pro Pro Gln Ser Pro Gln Gly Ala Ser Ala Phe
50                    55                    60

Pro Thr Thr Ile Asn Phe Thr Arg Gln Arg Gln Pro Ser Glu Gly Ser
65                    70                    75                    80

Ser Ser Arg Glu Glu Glu Gly Pro Ser Thr Ser Cys Ile Leu Glu Ser
          85                    90                    95

Leu Phe Arg Ala Val Ile Thr Lys Lys Val Ala Asp Leu Val Gly Phe
          100                  105                 110

Leu Leu Leu Lys Tyr Arg Ala Arg Glu Pro Val Thr Lys Ala Glu Met
          115                  120                 125

Leu Glu Ser Val Ile Lys Asn Tyr Lys His Cys Phe Pro Glu Ile Phe
          130                  135                 140

Gly Lys Ala Ser Glu Ser Leu Gln Leu Val Phe Gly Ile Asp Val Lys
145                  150                   155                 160

Glu Ala Asp Pro Thr Gly His Ser Tyr Val Leu Val Thr Cys Leu Gly

-continued

```
                165                 170                 175
Leu Ser Tyr Asp Gly Leu Leu Gly Asp Asn Gln Ile Met Pro Lys Thr
        180                 185                 190
Gly Phe Leu Ile Ile Val Leu Val Met Ile Ala Met Glu Gly Gly His
        195                 200                 205
Ala Pro Glu Glu Ile Trp Glu Glu Leu Ser Val Met Glu Val Tyr
    210                 215                 220
Asp Gly Arg Glu His Ser Ala Tyr Gly Glu Pro Arg Lys Leu Leu Thr
225                 230                 235                 240
Gln Asp Leu Val Gln Glu Lys Tyr Leu Glu Tyr Arg Gln Val Pro Asp
                245                 250                 255
Ser Asp Pro Ala Arg Tyr Glu Phe Leu Trp Gly Pro Arg Ala Leu Ala
        260                 265                 270
Glu Thr Ser Tyr Val Lys Val Leu Glu Tyr Val Ile Lys Val Ser Ala
        275                 280                 285
Arg Val Arg Phe Phe Phe Pro Ser Leu Arg Glu Ala Ala Leu Arg Glu
    290                 295                 300
Glu Glu Glu Gly Val
305             309
```

(2) INFORMATION FOR SEQ ID NO: 11:

(i) SEQUENCE CHARACTERISTICS:
    (A) LENGTH: 24 base pairs
    (B) TYPE: nucleic acid
    (C) STRANDEDNESS: single-stranded
    (D) TOPOLOGY: linear (xi) SEQUENCE DESCRIPTION: SEQ ID NO: 11:

AGCACTCTCC AGCCTCTCAC CGCA            24

(2) INFORMATION FOR SEQ ID NO: 12:

(i) SEQUENCE CHARACTERISTICS:
    (A) LENGTH: 24 base pairs
    (B) TYPE: nucleic acid
    (C) STRANDEDNESS: single-stranded
    (D) TOPOLOGY: linear (xi) SEQUENCE DESCRIPTION: SEQ ID NO: 12:

ACCGACGTCG ACTATCCATG AACA            24

(2) INFORMATION FOR SEQ ID NO: 13:

(i) SEQUENCE CHARACTERISTICS:
    (A) LENGTH: 24 base pairs
    (B) TYPE: nucleic acid
    (C) STRANDEDNESS: single-stranded
    (D) TOPOLOGY: linear (xi) SEQUENCE DESCRIPTION: SEQ ID NO: 13:

AGGCAACTGT GCTATCCGAG GGAA            24

(2) INFORMATION FOR SEQ ID NO: 14:

(i) SEQUENCE CHARACTERISTICS:
    (A) LENGTH: 8 base pairs
    (B) TYPE: nucleic acid
    (C) STRANDEDNESS: single-stranded
    (D) TOPOLOGY: linear (ix) FEATURE:
    (D) OTHER INFORMATION: BstX1 adapter lower strand (xi) SEQUENCE DESCRIPTION: SEQ ID NO: 14:

CTGGAAAG  8

(2) INFORMATION FOR SEQ ID NO: 15:

(i) SEQUENCE CHARACTERISTICS:
        (A) LENGTH: 18 base pairs
        (B) TYPE: nucleic acid
        (C) STRANDEDNESS: single-stranded
        (D) TOPOLOGY: linear (xi) SEQUENCE DESCRIPTION: SEQ ID NO: 15:

AGGCGCGAAT CAAGTTAG  18

(2) INFORMATION FOR SEQ ID NO: 16:

(i) SEQUENCE CHARACTERISTICS:
        (A) LENGTH: 18 base pairs
        (B) TYPE: nucleic acid
        (C) STRANDEDNESS: single-stranded
        (D) TOPOLOGY: linear (xi) SEQUENCE DESCRIPTION: SEQ ID NO: 16:

CTCCTCTGCT GTGCTGAC  18

(2) INFORMATION FOR SEQ ID NO: 17:

(i) SEQUENCE CHARACTERISTICS:
        (A) LENGTH: 20 base pairs
        (B) TYPE: nucleic acid
        (C) STRANDEDNESS: single-stranded
        (D) TOPOLOGY: linear (xi) SEQUENCE DESCRIPTION: SEQ ID NO: 17:

AGCTGCCTCT GGTTGGCAGA  20

(2) INFORMATION FOR SEQ ID NO: 18:

(i) SEQUENCE CHARACTERISTICS:
        (A) LENGTH: 1983 base pairs
        (B) TYPE: nucleic acid
        (C) STRANDEDNESS: double-stranded
        (D) TOPOLOGY: linear (xi) SEQUENCE DESCRIPTION: SEQ ID NO: 18:

```
TGGGAATCTG ACGGATCGGA GGCATTTGTG AGGAGGCGCG AATCAAGTTA GCGGGGGGAA   60
GAGTCTTAGA CCTGGCCAGT CCTCAGGGTG AGGGCCCTGA GGAAGAACTG AGGGACCTCC  120
CACCATAGAG AGAAGAAACC CCGGCCTGTA CTGCGCTGCC GTGAGACTGG TGCTCCAGGA  180
ACCAGGTGGT GACGAACTGG GTGTGAGGCA CACAGCCTAA AGTCAGCACA GCAGAGGAGG  240
CCCAGGCAGT GCCAGGAGTC AAGGCCTGTT GGATCTCATC ATCCATATCC CTGTTGATAC  300
GTTTACCTGC TGCTCCTGAA GAAGTCGTCA TGCCTCCCGT TCCAGGCGTT CCATTCCGCA  360
ACGTTGACAA CGACTCCCCG ACCTCAGTTG AGTTAGAAGA CTGGGTAGAT GCACAGCATC  420
CCACAGATGA GGAAGAGGAG GAAGCCTCCT CCGCCTCTTC CACTTTGTAC TTAGTATTTT  480
CCCCCTCTTC TTTCTCCACA TCCTCTTCTC TGATTCTTGG TGGTCCTGAG GAGGAGGAGG  540
TGCCCTCTGG TGTGATACCA AATCTTACCG AGAGCATTCC CAGTAGTCCT CCACAGGGTC  600
CTCCACAGGG TCCTTCCCAG AGTCCTCTGA GCTCCTGCTG CTCCTCTTTT TCATGGAGCT  660
CATTCAGTGA GGAGTCCAGC AGCCAGAAAG GGGAGGATAC AGGCACCTGT CAGGGCCTGC  720
```

```
CAGACAGTGA GTCCTCTTTC ACATATACAC TAGATGAAAA GGTGGCCGAG TTAGTGGAGT      780

TCCTGCTCCT CAAATACGAA GCAGAGGAGC CTGTAACAGA GGCAGAGATG CTGATGATTG      840

TCATCAAGTA CAAAGATTAC TTTCCTGTGA TACTCAAGAG AGCCCGTGAG TTCATGGAGC      900

TTCTTTTTGG CCTTGCCCTG ATAGAAGTGG GCCCTGACCA CTTCTGTGTG TTTGCAAACA      960

CAGTAGGCCT CACCGATGAG GGTAGTGATG ATGAGGGCAT GCCCGAGAAC AGCCTCCTGA     1020

TTATTATTCT GAGTGTGATC TTCATAAAGG GCAACTGTGC CTCTGAGGAG GTCATCTGGG     1080

AAGTGCTGAA TGCAGTAGGG GTATATGCTG GGAGGGAGCA CTTCGTCTAT GGGGAGCCTA     1140

GGGAGCTCCT CACTAAAGTT TGGGTGCAGG GACATTACCT GGAGTATCGG GAGGTGCCCC     1200

ACAGTTCTCC TCCATATTAT GAATTCCTGT GGGGTCCAAG AGCCCATTCA GAAAGCATCA     1260

AGAAGAAAGT ACTAGAGTTT TTAGCCAAGC TGAACAACAC TGTTCCTAGT TCCTTTCCAT     1320

CCTGGTACAA GGATGCTTTG AAAGATGTGG AAGAGAGAGT CCAGGCCACA ATTGATACCG     1380

CAGATGATGC CACTGTCATG GCCAGTGAAA GCCTCAGTGT CATGTCCAGC AACGTCTCCT     1440

TTTCTGAGTG AAGTCTAGGA TAGTTTCTTC CCCTTGTGTT TGAACAGGGC AGTTTAGGTT     1500

CTAGGTAGTG GAGGGCCAGG TGGGGCTCGA GGAACGTAGT GTTCTTTGCA TTTCTGTCCC     1560

ATATGGGTGA TGTAGAGATT TACCTGTTTT TCAGTATTTT CTAAATGCTT TTCCTTTGAA     1620

TAGCAGGTAG TTAGCTTCAG AGTGTTAATT TATGAATATT AGTCGACAT GTATTGCTCT      1680

TTATCTGGTT TAAGAGTAAC AGTTTGATAT TTTGTTAAAA AAATGGAAAT ACCTTCTCCC     1740

TTATTTTGTG ATCTGTAACA GGGTAGTGTG GTATTGTAAT AGGCATTTTT TTTTTTTTT      1800

ACAATGTGCA ATAACTCAGC AGTTAAATAG TGGAACAAAA TTGAAGGGTG GTCAGTAGTT     1860

TCATTTCCTT GTCCTGCTTA TTCTTTTGTT CTTGAAAATT ATATATACCT GGCTTTGCTT     1920

AGCTTGTTGA AGAAAGTAGC AGAAATTAAA TCTTAATAAA AGAAAAAAAA AAAAAAAAA      1980

AGG                                                                   1983
```

(2) INFORMATION FOR SEQ ID NO: 19:

(i) SEQUENCE CHARACTERISTICS:
        (A) LENGTH: 373
        (B) TYPE: amino acid
        (C) STRANDEDNESS: single-stranded
        (D) TOPOLOGY: linear (xi) SEQUENCE DESCRIPTION: SEQ ID NO: 19:

```
Met Pro Pro Val Pro Gly Val Pro Phe Arg Asn Val Asp Asn Asp Ser
                 5                  10                  15

Pro Thr Ser Val Glu Leu Glu Asp Trp Val Asp Ala Gln His Pro Thr
             20                  25                  30

Asp Glu Glu Glu Glu Ala Ser Ser Ala Ser Ser Thr Leu Tyr Leu
         35                  40                  45

Val Phe Ser Pro Ser Ser Phe Ser Thr Ser Ser Leu Ile Leu Gly
     50                  55                  60

Gly Pro Glu Glu Glu Val Pro Ser Gly Val Ile Pro Asn Leu Thr
 65                  70                  75                  80

Glu Ser Ile Pro Ser Ser Pro Pro Gln Gly Pro Gln Gly Pro Ser
                 85                  90                  95

Gln Ser Pro Leu Ser Ser Cys Cys Ser Ser Phe Ser Trp Ser Ser Phe
            100                 105                 110

Ser Glu Glu Ser Ser Ser Gln Lys Gly Glu Asp Thr Gly Thr Cys Gln
        115                 120                 125

Gly Leu Pro Asp Ser Glu Ser Ser Phe Thr Tyr Thr Leu Asp Glu Lys
```

```
                    130             135             140
Val Ala Glu Leu Val Glu Phe Leu Leu Lys Tyr Glu Ala Glu Glu
145                 150                 155                 160

Pro Val Thr Glu Ala Glu Met Leu Met Ile Val Ile Lys Tyr Lys Asp
                165                 170                 175

Tyr Phe Pro Val Ile Leu Lys Arg Ala Arg Glu Phe Met Glu Leu Leu
            180                 185                 190

Phe Gly Leu Ala Leu Ile Glu Val Gly Pro Asp His Phe Cys Val Phe
        195                 200                 205

Ala Asn Thr Val Gly Leu Thr Asp Glu Gly Ser Asp Asp Glu Gly Met
210                 215                 220

Pro Glu Asn Ser Leu Leu Ile Ile Ile Leu Ser Val Ile Phe Ile Lys
225                 230                 235                 240

Gly Asn Cys Ala Ser Glu Glu Val Ile Trp Glu Val Leu Asn Ala Val
                245                 250                 255

Gly Val Tyr Ala Gly Arg Glu His Phe Val Tyr Gly Glu Pro Arg Glu
                260                 265                 270

Leu Leu Thr Lys Val Trp Val Gln Gly His Tyr Leu Glu Tyr Arg Glu
275                 280                 285

Val Pro His Ser Ser Pro Pro Tyr Tyr Glu Phe Leu Trp Gly Pro Arg
290                 295                 300

Ala His Ser Glu Ser Ile Lys Lys Lys Val Leu Glu Phe Leu Ala Lys
305                 310                 315                 320

Leu Asn Asn Thr Val Pro Ser Ser Phe Pro Ser Trp Tyr Lys Asp Ala
                325                 330                 335

Leu Lys Asp Val Glu Glu Arg Val Gln Ala Thr Ile Asp Thr Ala Asp
            340                 345                 350

Asp Ala Thr Val Met Ala Ser Glu Ser Leu Ser Val Met Ser Ser Asn
            355                 360                 365

Val Ser Phe Ser Glu
    370

(2) INFORMATION FOR SEQ ID NO: 20:

(i) SEQUENCE CHARACTERISTICS:
        (A) LENGTH: 2940 base pairs
        (B) TYPE: nucleic acid
        (C) STRANDEDNESS: double-stranded
        (D) TOPOLOGY: linear (xi) SEQUENCE DESCRIPTION: SEQ ID NO: 20:

TGGGAATCTG ACGGATCGGA GGCATTTGTG AGGAGGCGCG AATCAAGTTA GCGGGGGGAA      60

GAGTCTTAGA CCTGGCCAGT CCTCAGGGTG AGGGCCCTGA GGAAGAACTG AGGGACCTCC     120

CACCATAGAG AGAAGAAACC CCGGCCTGTA CTGCGCTGCC GTGAGACTGG TAGGTCCCAG     180

ACAGGGAAAT GGCCCCAGAA GAAGGGAGGA GGTGCCGGCC CTCTAGGGAA TAAATAGGAA     240

GACACTGAGG AGGGCTGGGG GGAACGCCCC ACCTCAGAGG GCAGATTCCC AGAGATTCCC     300

ACCCTGCTCC TCAAGTATCA GCCCTCGTAG AGCTCCCCAG TCAGCTCAGG CGGGGTGGCA     360

GCCATCTTAT TCCTGGGTGA GTGGCGTAGG GGAGGCGGAG GCCTTGGTCT GAGGGTCCCA     420

TGGCAAGTCA GCACGGGGAG CTGCCTCTGG TTGGCAGAGG GAAGATTCCC AGGCCCTGCT     480

GGGGATAAGA CTGAGGAGTC ACATGTGCAT CAGAACGGAC GTGAGGCTAC CCCGACTGCC     540

CCCATGGTAG AGTGCTGGGA GGTGGCTGCC ACCGCCCTAC CTCCCACTGC TCTCAGGGAT     600

GTGGCGGTTG CTCTGAGGTT TGCCTTAGG CCAGCAGAGT GGTGGAGGCT CGGCCCTCTC      660
```

```
TGAGAAGCCG TGAAGTTGCT AATTAAATTC TGAGGGGGCC ATGCAGTCCA GAACTATGAG    720

GCTCTGGGAT TCTGGCCAGC CCCAGCTGTC AGCCCTAGCA GGCCCAAGAC CCTACTTGCA    780

GTCTTTAGCC TGAGGGGCTC CCTCACTTCC TCTTGCAGGT GCTCCAGGAA CCAGGTGGTG    840

ACGAACTGGG TGTGAGGCAC ACAGCCTAAA GTCAGCACAG CAGAGGAGGC CCAGGCAGTG    900

CCAGGAGTCA AGGTGAGTGC ACACCCTGGC TGTGTACCAA GGGCCCTACC CCCAGAAACA    960

GAGGAGACCC CACAGCACCC GGCCCTACCC ACCTATTGTC ACTCCTGGGG TCTCAGGCTC   1020

TGCCTGCCAG CTGTGCCCTG AGGTGTGTTC CCACATCCTC CTACAGGTTC CCAGCAGACA   1080

AACTCCCTAG GAAGACAGGA GACCTGTGAG GCCCTAGAGC ACCACCTTAA GAGAAGAAGA   1140

GCTGTAAGGT GGCCTTTGTC AGAGCCATCA TGGGTGAGTT TCTCAGCTGA GGCCACTCAC   1200

ACTGTCACTC TCTTCCACAG GCCTGTTGGA TCTCATCATC CATATCCCTG TTGATACGTT   1260

TACCTGCTGC TCCTGAAGAA GTCGTCATGC CTCCCGTTCC AGGCGTTCCA TTCCGCAACG   1320

TTGACAACGA CTCCCCGACC TCAGTTGAGT TAGAAGACTG GGTAGATGCA CAGCATCCCA   1380

CAGATGAGGA AGAGGAGGAA GCCTCCTCCG CCTCTTCCAC TTTGTACTTA GTATTTTCCC   1440

CCTCTTCTTT CTCCACATCC TCTTCTCTGA TTCTTGGTGG TCCTGAGGAG GAGGAGGTGC   1500

CCTCTGGTGT GATACCAAAT CTTACCGAGA GCATTCCCAG TAGTCCTCCA CAGGGTCCTC   1560

CACAGGGTCC TTCCCAGAGT CCTCTGAGCT CCTGCTGCTC CTCTTTTTCA TGGAGCTCAT   1620

TCAGTGAGGA GTCCAGCAGC CAGAAAGGGG AGGATACAGG CACCTGTCAG GGCCTGCCAG   1680

ACAGTGAGTC CTCTTTCACA TATACACTAG ATGAAAAGGT GGCCGAGTTA GTGGAGTTCC   1740

TGCTCCTCAA ATACGAAGCA GAGGAGCCTG TAACAGAGGC AGAGATGCTG ATGATTGTCA   1800

TCAAGTACAA AGATTACTTT CCTGTGATAC TCAAGAGAGC CCGTGAGTTC ATGGAGCTTC   1860

TTTTTGGCCT TGCCCTGATA GAAGTGGGCC CTGACCACTT CTGTGTGTTT GCAAACACAG   1920

TAGGCCTCAC CGATGAGGGT AGTGATGATG AGGGCATGCC CGAGAACAGC CTCCTGATTA   1980

TTATTCTGAG TGTGATCTTC ATAAAGGGCA ACTGTGCCTC TGAGGAGGTC ATCTGGGAAG   2040

TGCTGAATGC AGTAGGGGTA TATGCTGGGA GGGAGCACTT CGTCTATGGG GAGCCTAGGG   2100

AGCTCCTCAC TAAAGTTTGG GTGCAGGGAC ATTACCTGGA GTATCGGGAG GTGCCCCACA   2160

GTTCTCCTCC ATATTATGAA TTCCTGTGGG GTCAAGAGC CCATTCAGAA AGCATCAAGA    2220

AGAAAGTACT AGAGTTTTTA GCCAAGCTGA ACAACACTGT TCCTAGTTCC TTTCCATCCT   2280

GGTACAAGGA TGCTTTGAAA GATGTGGAAG AGAGAGTCCA GGCCACAATT GATACCGCAG   2340

ATGATGCCAC TGTCATGGCC AGTGAAAGCC TCAGTGTCAT GTCCAGCAAC GTCTCCTTTT   2400

CTGAGTGAAG TCTAGGATAG TTTCTTCCCC TTGTGTTTGA ACAGGGCAGT TTAGGTTCTA   2460

GGTAGTGGAG GGCCAGGTGG GGCTCGAGGA ACGTAGTGTT CTTTGCATTT CTGTCCCATA   2520

TGGGTGATGT AGAGATTTAC CTGTTTTTCA GTATTTTCTA AATGCTTTTC CTTTGAATAG   2580

CAGGTAGTTA GCTTCAGAGT GTTAATTTAT GAATATTAGT CGCACATGTA TTGCTCTTTA   2640

TCTGGTTTAA GAGTAACAGT TTGATATTTT GTTAAAAAAA TGGAAATACC TTCTCCCTTA   2700

TTTTGTGATC TGTAACAGGG TAGTGTGGTA TTGTAATAGG CATTTTTTTT TTTTTTTACA   2760

ATGTGCAATA ACTCAGCAGT TAAATAGTGG AACAAAATTG AAGGGTGGTC AGTAGTTTCA   2820

TTTCCTTGTC CTGCTTATTC TTTTGTTCTT GAAAATTATA TATACCTGGC TTTGCTTAGC   2880

TTGTTGAAGA AAGTAGCAGA AATTAAATCT TAATAAAAGA AAAAAAAAAA AAAAAAAGG   2940
```